US010820913B2

(12) United States Patent
Miller et al.

(10) Patent No.: US 10,820,913 B2
(45) Date of Patent: Nov. 3, 2020

(54) INTRAOSSEOUS DEVICE HANDLES, SYSTEMS, AND METHODS

(71) Applicant: TELEFLEX LIFE SCIENCES LIMITED, Valletta (MT)

(72) Inventors: Larry J. Miller, Shavano Park, TX (US); John Morgan, Shavano Park, TX (US); Robert W. Titkemeyer, Shavano Park, TX (US); Chris Kilcoin, Shavano Park, TX (US)

(73) Assignee: TELEFLEX LIFE SCIENCES LIMITED, Valletta (MT)

( * ) Notice: Subject to any disclaimer, the term of this patent is extended or adjusted under 35 U.S.C. 154(b) by 1182 days.

(21) Appl. No.: 14/776,014

(22) PCT Filed: Mar. 15, 2013

(86) PCT No.: PCT/US2013/031928
§ 371 (c)(1),
(2) Date: Sep. 14, 2015

(87) PCT Pub. No.: WO2014/142948
PCT Pub. Date: Sep. 18, 2014

(65) Prior Publication Data
US 2016/0022282 A1     Jan. 28, 2016

(51) Int. Cl.
*A61B 17/16*     (2006.01)
*A61B 17/32*     (2006.01)
(Continued)

(52) U.S. Cl.
CPC ........ *A61B 17/1637* (2013.01); *A61B 10/025* (2013.01); *A61B 17/162* (2013.01); *A61B 17/1615* (2013.01); *A61B 17/1622* (2013.01); *A61B 17/32002* (2013.01); *A61B 10/0283* (2013.01); *A61B 2010/0208* (2013.01);
(Continued)

(58) Field of Classification Search
CPC ............ A61B 17/1637; A61B 17/1615; A61B 17/162; A61B 17/1622; A61B 17/32002; A61B 10/025; A61B 2050/3008; A61B 2050/3006; A61B 2010/0208; A61B 2017/00473; A61B 2017/00477; A61B 2010/0258; A61B 10/0283
See application file for complete search history.

(56) References Cited

U.S. PATENT DOCUMENTS

| 4,630,616 A | 12/1986 | Tretinyak ................... 600/566 |
| 4,655,226 A | 4/1987 | Lee ............................. 600/567 |

(Continued)

FOREIGN PATENT DOCUMENTS

| EP | 754431 | 1/1997 |
| EP | 992218 | 4/2000 |

(Continued)

OTHER PUBLICATIONS

International Search Report and Written Opinion Issued in PCT/US2013/031928, dated Dec. 11, 2013.

*Primary Examiner* — Rene T Towa
(74) *Attorney, Agent, or Firm* — BakerHostetler

(57) ABSTRACT

Handles configured to be removably coupled to IO devices that are also configured to be coupled to powered drivers. Kits including IO devices and the present handles. Methods of using the present handles and IO devices.

26 Claims, 21 Drawing Sheets

(51) Int. Cl.
  *A61B 17/00* (2006.01)
  *A61B 50/30* (2016.01)
  *A61B 10/02* (2006.01)
(52) U.S. Cl.
  CPC ............... *A61B 2010/0258* (2013.01); *A61B 2017/00473* (2013.01); *A61B 2017/00477* (2013.01); *A61B 2050/3006* (2016.02); *A61B 2050/3008* (2016.02)

(56) References Cited

U.S. PATENT DOCUMENTS

| | | |
|---|---|---|
| 4,793,363 A | 12/1988 | Ausherman et al. ......... 600/567 |
| 4,838,282 A | 6/1989 | Strasser et al. ............ 600/567 |
| 5,357,974 A | 10/1994 | Baldridge .................. 600/567 |
| 5,385,151 A | 1/1995 | Scarfone et al. ............ 600/567 |
| 5,522,398 A * | 6/1996 | Goldenberg ......... A61B 10/025 600/562 |
| 5,634,473 A * | 6/1997 | Goldenberg ......... A61B 10/025 600/567 |
| 5,758,655 A | 6/1998 | Como et al. ................ 600/562 |
| 6,221,029 B1 | 4/2001 | Mathis et al. .............. 600/564 |
| 6,312,394 B1 | 11/2001 | Fleming .................... 600/567 |
| 6,340,351 B1 * | 1/2002 | Goldenberg ......... A61B 10/025 403/292 |
| 6,443,910 B1 | 9/2002 | Krueger et al. ............. 600/567 |
| 6,916,292 B2 | 7/2005 | Morawski et al. ........... 600/567 |
| 7,278,972 B2 | 10/2007 | Lamoureux et al. .......... 600/567 |
| RE40,796 E | 6/2009 | O'Neill .................... 600/567 |
| 2001/0009978 A1 | 7/2001 | Krueger et al. ............. 600/567 |
| 2004/0077973 A1 | 4/2004 | Groenke et al. ............. 600/567 |
| 2004/0127814 A1 | 7/2004 | Negroni .................... 600/567 |
| 2004/0191897 A1 | 9/2004 | Muschler ................... 435/325 |
| 2005/0165404 A1 | 7/2005 | Miller ....................... 606/80 |
| 2005/0267383 A1 | 12/2005 | Groenke et al. ............. 600/567 |
| 2007/0010843 A1 | 1/2007 | Green ....................... 606/185 |
| 2007/0197935 A1 | 8/2007 | Reiley et al. ............... 600/567 |
| 2007/0260255 A1 * | 11/2007 | Haddock ............ A61B 17/3421 606/80 |
| 2007/0265548 A1 | 11/2007 | Goldenberg ................. 600/567 |
| 2007/0270775 A1 | 11/2007 | Miller et al. ................ 604/506 |
| 2008/0045860 A1 * | 2/2008 | Miller ................. A61B 10/025 600/567 |
| 2008/0119759 A1 | 5/2008 | McLain ..................... 600/567 |
| 2008/0262383 A1 | 10/2008 | Routhier et al. ............. 600/567 |
| 2009/0082697 A1 | 3/2009 | Goldenberg ................. 600/567 |
| 2010/0004626 A1 | 1/2010 | Miller et al. ................ 604/506 |
| 2010/0234761 A1 | 9/2010 | Cortes et al. ............... 600/567 |
| 2010/0298784 A1 | 11/2010 | Miller ...................... 604/272 |
| 2011/0054537 A1 * | 3/2011 | Miller ................ A61B 17/1655 606/279 |
| 2012/0035501 A1 | 2/2012 | Landrigan et al. ........... 600/567 |

FOREIGN PATENT DOCUMENTS

| | | |
|---|---|---|
| EP | 1428476 | 1/2008 |
| EP | 1087706 | 5/2009 |
| EP | 1967142 | 8/2010 |
| EP | 1421907 | 10/2010 |
| EP | 1691696 | 1/2011 |
| JP | 04338470 | 11/1992 |
| JP | 2004154582 | 6/2004 |
| JP | 2008237302 | 10/2008 |
| JP | 2010-46504 A | 3/2010 |
| KR | 20080069517 A | 7/2008 |
| WO | WO 9603081 | 2/1996 |
| WO | WO 0016824 | 3/2000 |
| WO | WO 0044286 | 8/2000 |
| WO | WO 0056220 | 9/2000 |
| WO | WO 0178590 | 10/2001 |
| WO | WO 2005009246 | 2/2005 |
| WO | WO 2005072625 | 8/2005 |
| WO | WO 2008033874 | 3/2008 |
| WO | WO 2009031880 | 3/2009 |

\* cited by examiner

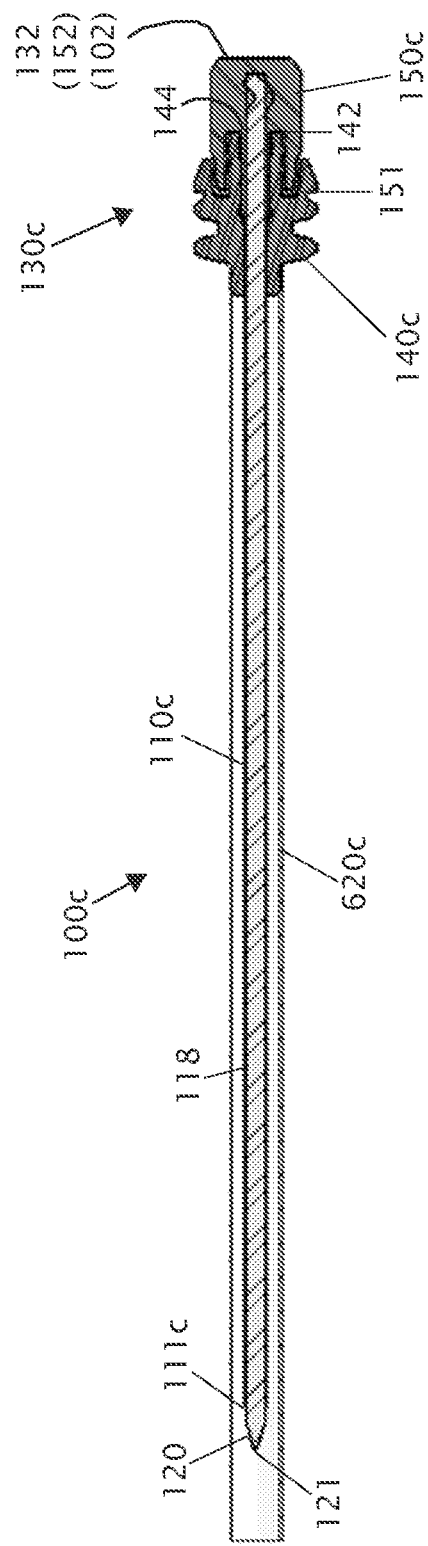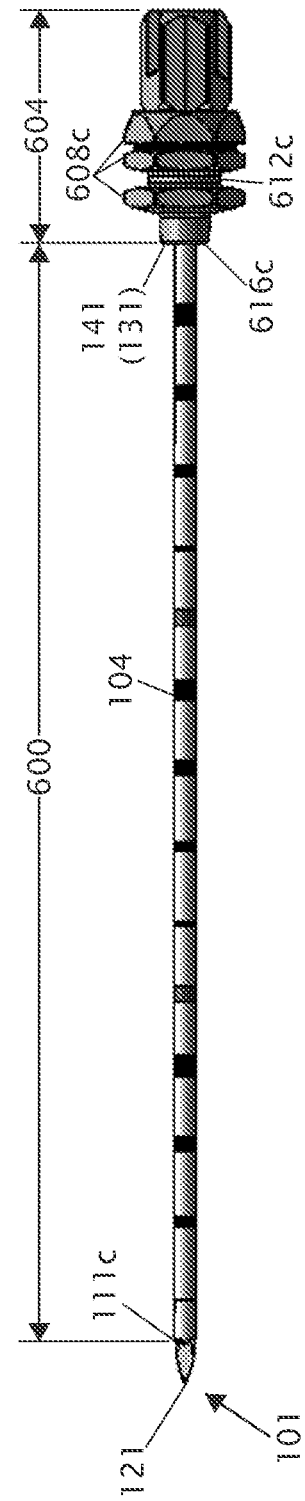
FIG. 8A
FIG. 8B

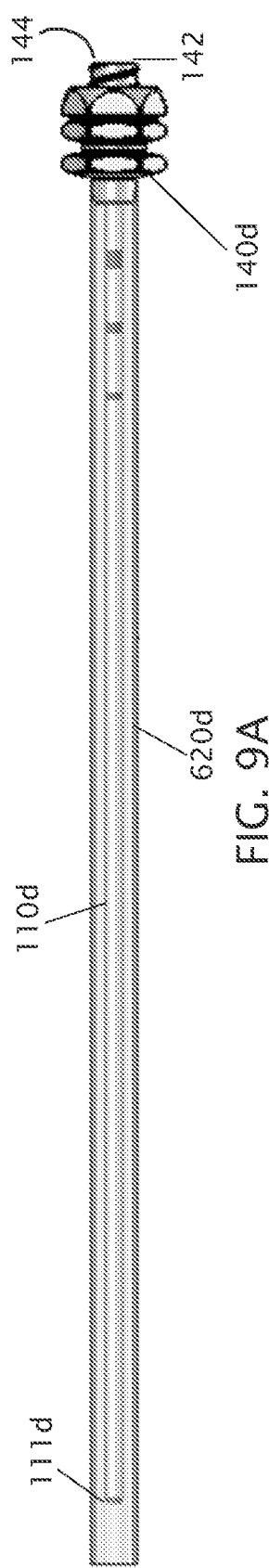
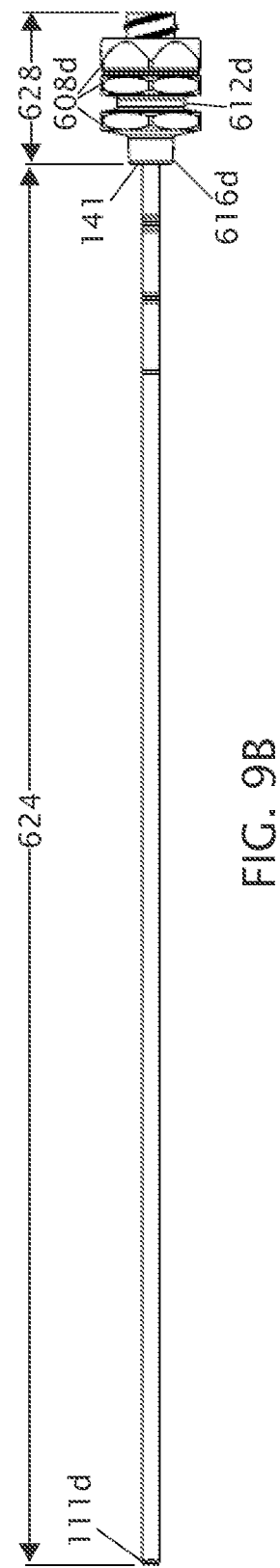
FIG. 9A
FIG. 9B

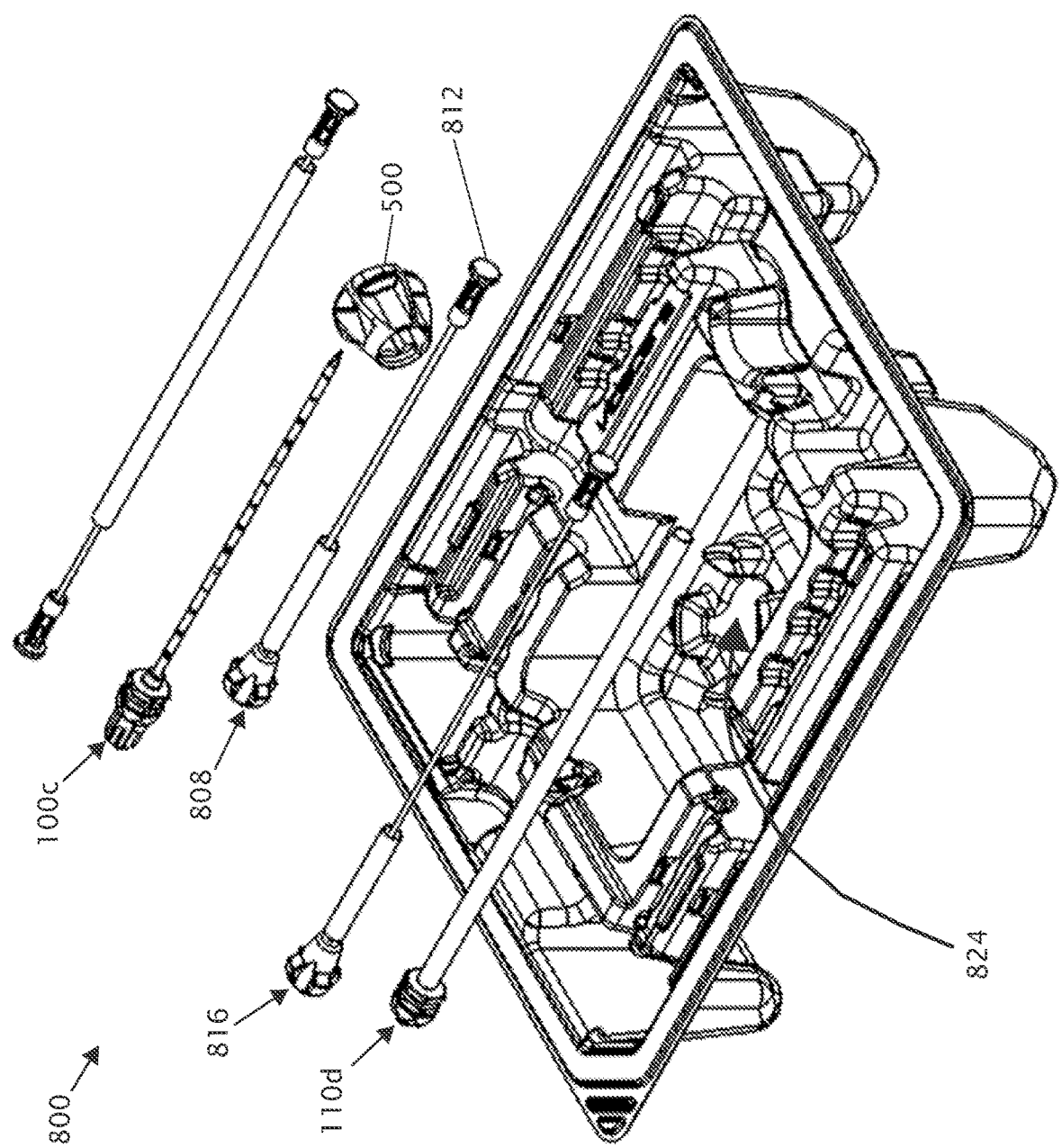

INTRAOSSEOUS DEVICE HANDLES, SYSTEMS, AND METHODS

CROSS REFERENCE TO RELATED APPLICATIONS

This application is a national phase application under 35 U.S.C. § 371 of International Application No. PCT/US2013/031928, filed Mar. 15, 2013, which is incorporated by reference herein in its entirety without disclaimer.

BACKGROUND

1. Field of the Invention

The present invention relates generally to intraosseous (IO) access and, more particularly, but not by way of limitation, to device handles, systems, and methods for IO access (e.g., to obtain bone marrow from the bone of a patient for biopsy and/or transplantation).

2. Description of Related Art

Examples of intraosseous devices, powered drivers, and couplers for coupling IO devices to powered drivers are disclosed in International Patent PCT/US2007/078207 (published as WO 2008/033874).

SUMMARY

This disclosure includes embodiments of apparatuses, kits, and methods.

Some embodiments of the present apparatuses comprise a handle configured to be removably coupled to a hub of an intraosseous device, the handle having a body defining a passage through the body, at least a portion of the passage having a non-circular cross-sectional shape configured to receive the hub and prevent the hub from rotating relative to the handle, the body including one or more resilient arms each having a projection extending inward toward a rotational axis of the handle to resist removal of the hub if the hub is disposed in the passage, each of the one or more resilient arms configured to be deflected away from a rotational axis of the handle to permit insertion and removal of the hub. In some embodiments, a cross-sectional perimeter of the handle has a first transverse dimension that is perpendicular to a longitudinal axis of the passage, and a second transverse dimension that is perpendicular to the first transverse dimension, and where the first transverse dimension does not vary from the second transverse dimension by more than ten percent of the first transverse dimension. In some embodiments, the handle has a cross-sectional perimeter that is substantially circular. In some embodiments, the one or more resilient arms include two resilient arms on opposite sides of the passage, each of the two resilient arms having a length extending parallel to the longitudinal axis of the passage. In some embodiments, the non-circular cross section is hexagonal.

Some embodiments of the present apparatuses (e.g., for accessing bone) comprise a first hub configured to be removably coupled to a driveshaft of a powered driver; a cannula having a first end configured to penetrate bone, a second end coupled in fixed relation to the hub, and a channel extending between the first end and the second end; a handle configured to be removably coupled to the hub such that a user can grasp the handle to manipulate the cannula by hand, where the hub is not configured to be simultaneously coupled to a driveshaft and the handle. In some embodiments, the first end of the cannula has an oval cross-sectional shape. In some embodiments, the hub has a connector and is coupled to the second end of the cannula such that the connector is in fluid communication with the channel of the cannula.

Some embodiments of the present apparatuses (e.g., for accessing bone) comprise a first hub configured to be removably coupled to a driveshaft of a powered driver; a first cannula having a first end configured to penetrate bone, a second end coupled in fixed relation to the hub, and a channel extending between the first end and the second end, the channel having a first inner transverse dimension; a second hub configured to be removably coupled to a driveshaft of a powered driver; a second cannula having a first end configured to extract a bone marrow sample, a second end coupled in fixed relation to the second hub, and a channel extending between the first end and the second end, the second cannula having an outer transverse dimension that is smaller than the inner transverse dimension of the channel of the first cannula such that the second cannula can be inserted into the channel of the first cannula and rotated relative to the first cannula; a handle configured to be removably coupled to the second hub such that a user can grasp the handle to manipulate the second cannula by hand, where the second hub is not configured to be simultaneously coupled to a driveshaft and the handle. In some embodiments, the first end of the second cannula has an oval cross-sectional shape. In some embodiments, the second cannula has a length that is greater than a length of the first cannula.

In some embodiments of the present apparatuses, the first hub has a connector and is coupled to the second end of the first cannula such that the connector is in fluid communication with the channel of the first cannula. In some embodiments, the second hub has a connector and is coupled to the second end of the second cannula such that the connector is in fluid communication with the channel of the second cannula. In some embodiments, the first hub has a hexagonal cross-section. In some embodiments, the second hub has a hexagonal cross-section. In some embodiments, the first hub has an outer surface defining one or more detents. In some embodiments, the second hub has an outer surface defining one or more detents. In some embodiments, the handle comprises a body defining a passage having a length and a non-circular cross-sectional shape; one or more projections extending toward the center of the passage to resist removal of the hub if the hub is disposed in the passage. In some embodiments, the interior region has a hexagonal cross-section.

In some embodiments of the present apparatuses, the handle comprises one or more resilient arms, each having a first end coupled in fixed relation to the body, and a second end extending from the first end such that the second end is movable toward a rotational axis of the handle, where the one or more protrusions are each coupled to different one of the second ends of the of the one or more resilient arms, and where each of the resilient arms is configured to be deflected away from the rotation axis of the handle to permit insertion and removal of the hub. In some embodiments, the body further comprises a plurality of ribs. In some embodiments, the ribs comprise a plurality of longitudinal ribs extending parallel to the rotational axis of the handle, and at least one circumferential rib extending between longitudinal ribs. In some embodiments, each rib has a distal edge, and the ribs are configured such that a circle disposed in a plane that is perpendicular to the rotational axis contacts the distal edges of at least three ribs. In some embodiments, the handle has a first end and a second end, and the body defines an opening in the second end that has at least one transverse dimension that is smaller than a corresponding transverse dimension of the passage. In some embodiments, the body defines a hollow entry portion at the first end of the coupler, the entry portion having a cross-sectional area that is larger than the cross-sectional area of the interior region. In some embodiments, the entry portion has a circular cross-section.

Some embodiments of the present kits comprise an apparatus with any of the features previously described and a tray within which the apparatus is sealed. In some embodiments, a kit can comprise a coupler assembly having a first end configured to be removably coupled to a hub such that rotation of the coupler assembly will cause rotation of the hub, the coupler assembly having a second end configured to be removably coupled to the driveshaft of the powered driver, where the hub is configured to be coupled to the driveshaft via the coupler. In some embodiments, the first end of the coupler assembly is configured to be removably coupled to either of the first hub and the second hub. In some embodiments, a kit can comprise a powered driver having a driveshaft. In some embodiments, a kit can comprise a tray within which the apparatus is sealed.

Some embodiments of the present methods comprise inserting the first cannula of an apparatus into a bone using a powered driver that is coupled to the first hub; de-coupling the powered driver from the first hub; coupling the handle to the first hub; and manipulating the first cannula via the handle.

Some embodiments of the present methods comprise inserting the first cannula of an apparatus into a bone using a powered driver that is coupled to the first hub; de-coupling the powered driver from the first hub; and coupling the handle to the second hub; disposing the second cannula in the channel of the first cannula; and manipulating the second cannula via the handle.

Any embodiment of any of the devices, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The embodiments of the present snap handles, coupler assemblies, drivers, intraosseous (IO) devices, and their components shown in the figures are drawn to scale for at least the embodiments shown.

FIGS. 8A and 8B depict cross-sectional and side views of another embodiment of the present IO devices including a cannula and a trocar.

FIGS. 9A and 9B depict side views of another embodiment of the present IO devices including a cannula that is useable with and insertable into the cannula of the device of FIGS. 9A-9B.

FIG. 21 depicts an exploded perspective view the medical procedure tray of FIGS. 19 and 20.

DESCRIPTION OF ILLUSTRATIVE EMBODIMENTS

Figure 1A:
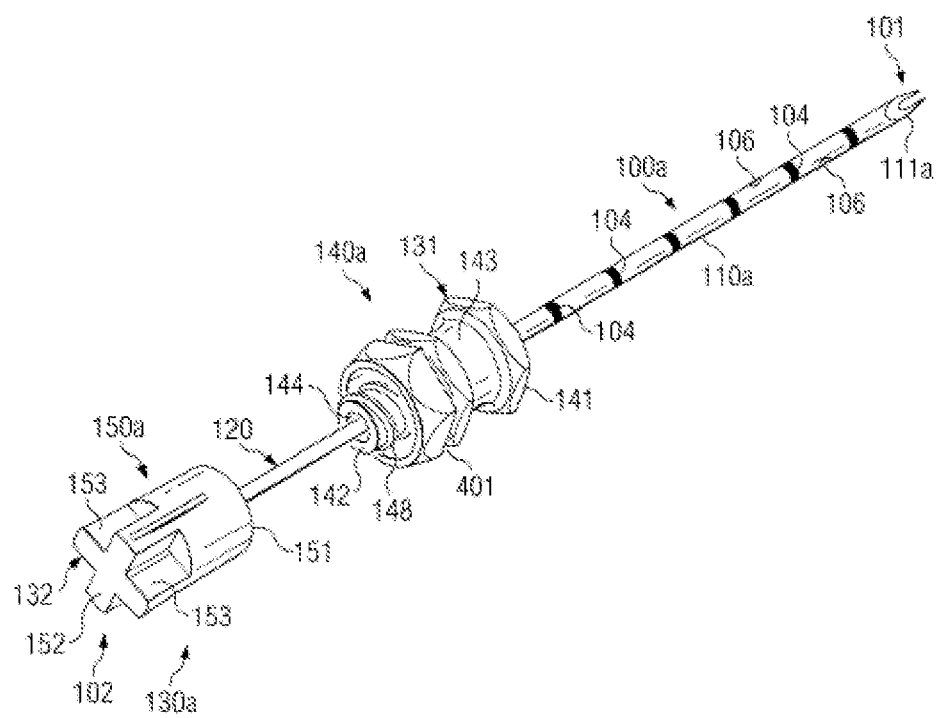
FIG. 1A depicts a perspective view of one embodiment of the present intraosseous devices having a first embodiment of a cannula and a first embodiment of a stylet.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a snap handle or other device that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Further, a device or system that is configured in a certain way is configured in at least that way, but it can also be configured in other ways than those specifically described.

Various types of coupler assemblies incorporating teachings of the present disclosure may be satisfactorily used to releasably engage one end of a shaft extending from a driver with one end of an intraosseous device. For some embodiments the powered driver may include a driveshaft having one end with a generally hexagonal cross section operable to be releasably engaged with a latch mechanism disposed in one end of a coupler assembly. For some embodiments a coupler assembly incorporating teachings of the present disclosure may be referred to as a "hands free" coupler, a quick disconnect or quick release coupler and/or port assembly.

Embodiments of the present powered drivers may be used to insert an IO device incorporating teachings of the present disclosure into a selected target area or target site in ten seconds or less. However, various teachings of the present disclosure are not limited to use with powered drivers. Manual drivers and spring powered drivers may also be used with IO devices incorporating teachings of the present disclosure.

Examples of manual drivers are shown in co-pending patent application Ser. No. 11/042,912 entitled Manual Intraosseous Device filed Jan. 25, 2005 (published as US 2005/0165404). The term "fluid" may be used in this application to include liquids such as, but not limited to, blood, water, saline solutions, IV solutions, plasma, or any mixture of liquids, particulate matter, dissolved medication, and/or drugs associated with biopsy or aspiration of bone marrow or communication of fluids with bone marrow or other target sites. The term "fluid" may also be used in this patent application to include any body fluids and/or liquids containing particulate matter such as bone marrow and/or cells which may be withdrawn from a target area.

The terms "harvest" and "harvesting" may be used in this application to include bone and/or bone marrow biopsy and bone marrow aspiration. Bone and/or bone marrow biopsy (sometimes referred to as "needle biopsy") may be generally described as removing a relatively small piece or specimen of bone and/or bone marrow from a selected target area for biopsy purposes. Bone marrow aspiration (sometimes referred to as "bone marrow sampling") may be generally described as removing larger quantities of bone marrow from a selected target area. Relatively large quantities of bone marrow may be used for diagnostic, transplantation, and/or research purposes. For example some stem cell research techniques may require relatively large quantities of bone marrow.

The term "insertion site" may be used in this application to describe a location on a bone at which an intraosseous device may be inserted or drilled into the bone and associated bone marrow. Insertion sites are generally covered by skin and soft tissue. The term "target area" refers to any location on or within biological material, such as the biological material of a living human being.

The term "intraosseous (IO) device" may be used in this application to include, but is not limited to, any hollow needle, hollow drill bit, penetrator assembly, bone penetrator, catheter, cannula, trocar, stylet, inner penetrator, outer penetrator, IO needle, biopsy needle, aspiration needle, IO needle set, biopsy needle set or aspiration needle set operable to access or provide access to an intraosseous space or interior portions of a bone. Such IO devices may be formed, at least in part, from metal alloys such as 304 stainless steel and other biocompatible materials associated with needles and similar medical devices.

Embodiments of the present drivers and drive systems can be included in medical procedure trays such as those disclosed in International Patent Application No. PCT/US2007/078207 (published as WO 2008/033874).

The devices and components shown in FIGS. 1A to 7C are prior art devices and components, and the following description of them is provided to give the reader context for the types of devices and components that can be used consistently with embodiments of the present drivers, drive systems, and kits.

Referring now to the drawings, and more particularly to FIG. 1A, shown therein and designated by the reference numeral 100*a* is one embodiment of the present intraosseous (IO) needle sets or aspiration needle sets. Aspiration needle set 100*a* comprises a hollow outer penetrator or cannula 110*a*, a corresponding inner penetrator or stylet (or trocar) 120, and a hub assembly 130*a*. In the embodiment shown, first end 111*a* of cannula 110*a* and first end 121 of stylet 120 are operable or configured to penetrate a bone and associated bone marrow. Various features of first end 111*a* of cannula 110*a* and first end 121 of stylet 120 are shown in more detail in FIGS. 1B-1D. First end 101 of IO needle set 100*a* corresponds generally with first end 111*a* of cannula 110*a* and first end 121 of stylet 120.

In the embodiment shown, cannula 110*a* includes a plurality of markings 104 disposed on exterior portions of the cannula. Markings 104 may be referred to as "positioning marks" or "depth indicators," and may be used to indicate the depth of penetration of needle set 100*a* into a bone and associated bone marrow. In some embodiments, cannula 110*a* may have a length of approximately sixty (60) millimeters and/or a nominal outside diameter of approximately 0.017 inches (e.g., corresponding generally to the dimensions of a sixteen (16) gauge needle). Cannula 110*a* and/or stylet 120 may be formed from stainless steel or other suitable biocompatible materials. In some embodiments, markings 104 are spaced at one (1) centimeter intervals on exterior portions of cannula 110*a*. In some embodiments, one or more side ports 106 may be formed in exterior portions of cannula 110*a* spaced from first end 111*a*.

Hub assembly 130*a* may be configured and/or used to releasably dispose stylet 120 within the longitudinal bore or lumen of cannula 110*a*. In the embodiment shown, hub assembly 130*a* includes a first hub 140*a* and a second hub 150*a*. A second end of cannula 110*a*, opposite from first end 111*a*, may be securely engaged with hub 140*a*. The second end of stylet 120, opposite from first end 121, may be securely engaged with the first end of hub 150*a*. As shown in FIG. 1A, cannula 110*a* may extend longitudinally from first end 141 of hub 140a. Stylet 120 may also extend from the first end of hub 150a. The second end of hub 140a may include a standard Luer lock fitting which may be releasably engaged with a corresponding Luer lock fitting disposed within the first end of second hub 150a. The Luer lock fitting disposed on the second end of hub 140a may be in fluid communication with the bore or passage in cannula 110a, and may be operable to be releasably engaged with a standard syringe type fitting and/or a standard intravenous (IV) connection. In the embodiment shown, hub 150a includes second end 152 that generally corresponds with second end 132 of hub assembly 130a and second end 102 of IO needle set 100a. Hub 140a may include first end 141 which may generally correspond with first end 131 of hub assembly 130a. Cannula 110a may extend longitudinally from first end 141 of hub 140a and first end 131 of hub assembly 130.

Figure 6C:
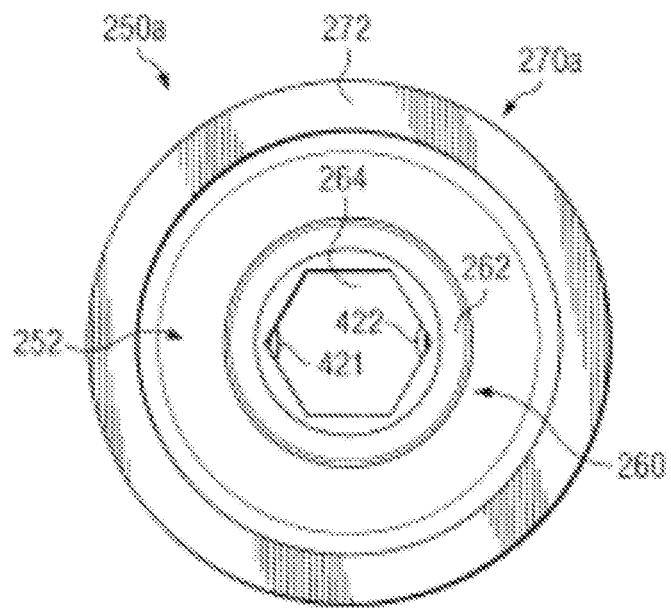
FIGS. 6A-6C depict various views of the coupler assembly of FIG. 3.
Figure 6A:
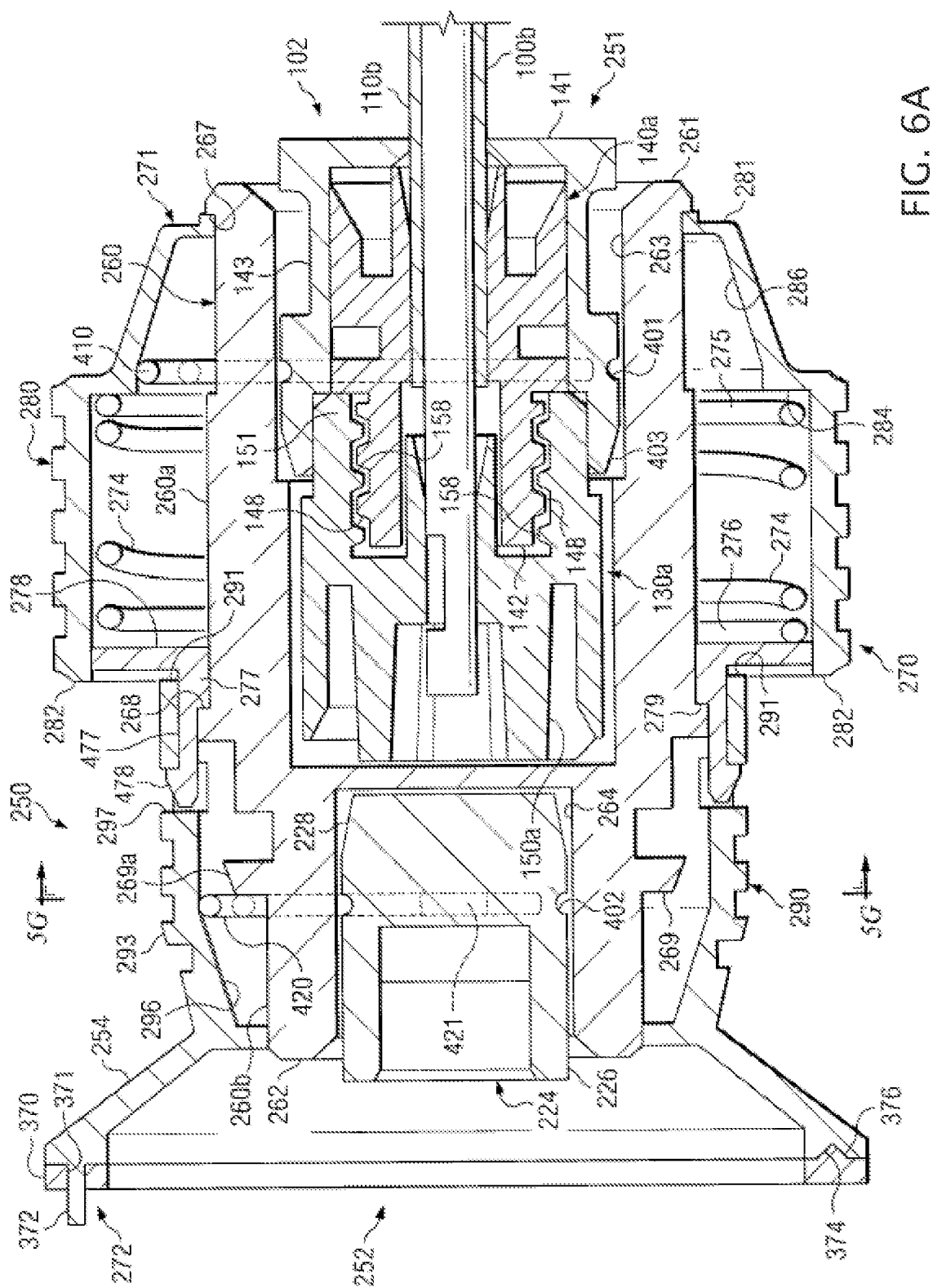
Figure 6B:
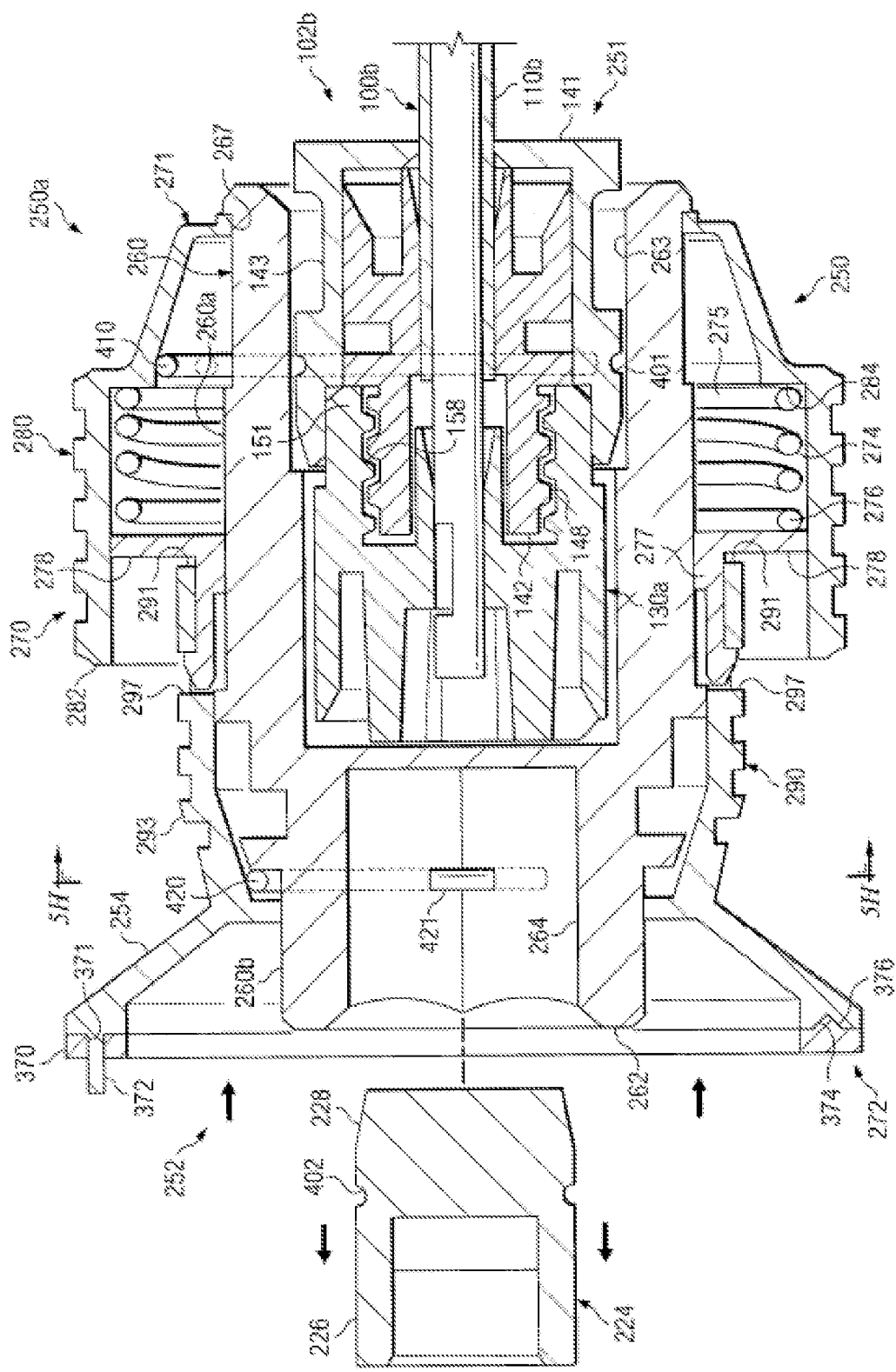

In the embodiment shown, the second end of a hub assembly may be operable to be disposed within a receptacle formed in a coupler assembly, as described in more detail below. One feature of the present disclosure may include forming a hub assembly which may be releasably engaged within a first receptacle disposed in a first end of a coupler assembly (e.g., receptacle 263 proximate first end 261 of elongated core 260 as shown in FIGS. 6A-6B). The dimensions and configuration of receptacle 263 may be selected to prevent rotation of hub 150a relative to hub 140a if hub assembly 130a is disposed in receptacle 263 (e.g., while inserting (rotating) an IO device into a bone and associated bone marrow). A powered driver may be releasably engaged with a second receptacle disposed in a second end of the coupler assembly (e.g., receptacle 264 proximate second end 262 of elongated core 260 as shown in FIGS. 6A-6B).

In the embodiment shown, intraosseous device or aspiration needle set 100a includes first end 151 of hub 150a spaced from second end 142 of hub 140a. Portions of stylet 120 extending from first end 151 of hub 150a are shown slidably disposed within lumen or longitudinal bore 118 of cannula 110a. Hub assembly 130a may include first end 131 which may correspond generally with first end 141 of hub 140a. Hub assembly 130a may also include second end 132 which may correspond generally with second end 152 of hub 150a and second end 102 of hub assembly 130a, as shown. Cannula 110a may be attached to and extend from first end 141 of hub 140a. Second end 142 of hub 140a may include one-half a typical Luer lock connection or fitting operable to be releasably engaged with corresponding portions of a Luer lock connection or fitting disposed in first end 151 of second hub 150a. For embodiments such as the one shown in FIG. 1A, first end 131 of hub assembly 130a may correspond with first end 141 of first hub 140a. Second end 152 of second hub 150a may correspond with second end 132 of hub assembly 130a and second end 102 of aspiration needle set 100a.

At least one portion of hub assembly 130a may have a generally hexagonal cross section operable to be received within the generally hexagonal cross section of receptacle 263 disposed proximate first end 251 of coupler assembly 250, as shown in FIGS. 6A-6B. For some embodiments, portions of first hub 140a disposed adjacent to reduced outside diameter portion 143 may have generally hexagonal cross sections, as shown in FIG. 1A. In other embodiments, various cross sections other than hexagonal may be satisfactorily used to releasably engage a powered driver with one end of a coupler assembly and an intraosseous device with an opposite end of the coupler assembly. Aspiration needle sets may include a trocar, stylet, or penetrator in combination with an associated cannula, catheter or outer penetrator. However, biopsy needles formed in accordance with teachings of the present disclosure may or may not include a trocar, stylet, or inner penetrator.

Hub 140a may include second end 142 with opening 144 formed therein. A passageway may extend from second end 142 towards first end 141 of hub 140a, as illustrated in FIGS. 6A-6B. A passageway may be operable to communicate fluids with lumen 118 of cannula 100a. Second end 142 of hub 140 may include various features of a conventional Luer lock connection or fitting, including threads 148, and corresponding threads 158 may be formed within first end 151 of hub 150a, as shown in FIGS. 6A-6B.

For some applications hub 140a and hub 150a may, for example, be formed using injection molding techniques. For such embodiments hub 140a may include reduced outside diameter portion 143 disposed between first end 141 and second end 142. In a similar manner a plurality of void spaces or cutouts 153 may be formed in hub 150a adjacent to and extending from second end 152 in the direction of first end 151. The configuration and dimensions of reduced diameter portion 143 and/or cutouts 153 may be varied to optimize associated injection molding techniques and at the same time provide required configurations, dimensions and material strength to allow associated hub assembly 130a to function as described in this disclosure.

In some embodiments, tip 123 of stylet 120 may be disposed relatively close to a tip of cannula 110a. For some applications, first end 121 of stylet 120 and first end 111a of cannula 110a may be ground at the same time to form adjacent cutting surfaces. Grinding ends 111a and 121 at the same time may result in forming a single cutting unit to form generally matching cutting edges. Other types of cutting surfaces formed in accordance with teachings of the present disclosure may be discussed later (e.g., as described with reference to FIGS. 1B-1D).

Figure 1B:
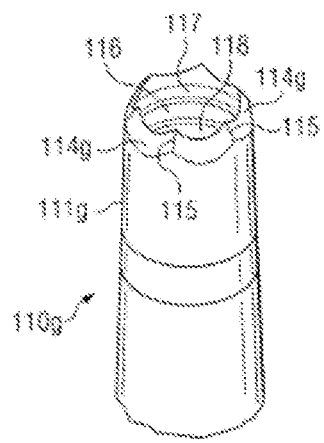
FIG. 1B depicts a perspective view of a second embodiment of the present cannulas.
Figure 1C:
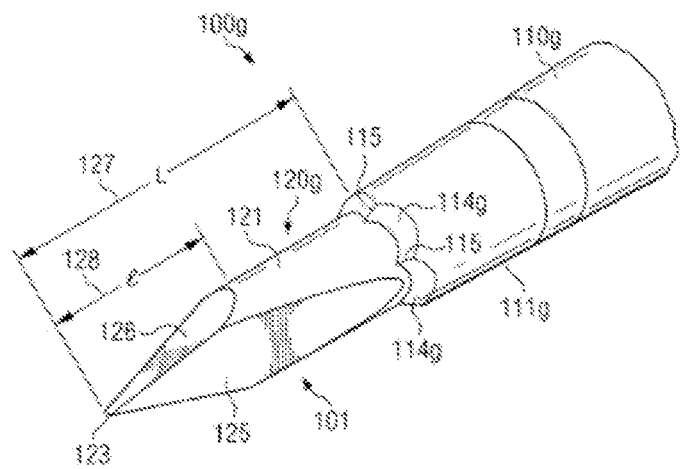
FIGS. 1C and 1D depict a perspective views of a second embodiment of the present IO devices having a second embodiment of the present stylets disposed in the cannula of FIG. 2.
Figure 1D:
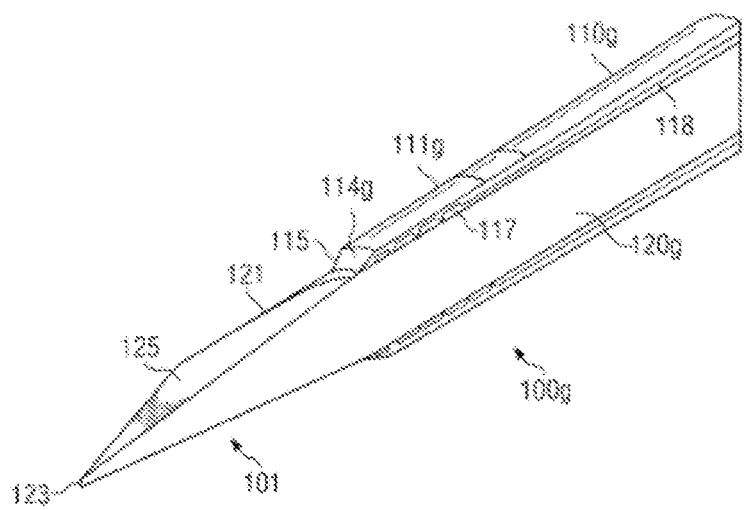

FIGS. 1B-1D show a second example of cutting surfaces and tips which may be formed adjacent to the ends of a cannula and/or an associated stylet in the present embodiments. In the embodiment shown, outer penetrator or cannula 110g may include first end 111g having a plurality of cutting surfaces 114g formed adjacent to opening 116 in first end 111g. Opening 116 may communicate with and form a portion of an associated longitudinal bore or lumen 118. For some applications cutting surfaces 114g may be formed using electrical discharge machining (EDM) techniques or otherwise, as described in WO 2008/033874. In the embodiment shown, first end 111g has a generally tapered configuration or reduced outside diameter as compared with other portions of cannula 110g In other embodiments, first end 111g has an outside diameter that is equal to the outside diameter of other portions of cannula 110g (e.g., cannula 110g can have a constant outside diameter along the entire length of the cannula). Cutting surfaces 114g may, for example, be formed using machine grinding techniques. In some embodiments, such as the one shown, end 111g of cannula 110g may include six ground cutting surfaces 114g with respective crowns 115 therebetween. Forming a biopsy needle set and/or biopsy needle with tapered end 111g and a plurality of cutting surfaces 114g and crowns 115 may provide improved drilling performance (e.g., relative to others configurations) when the resulting biopsy needle set and/or biopsy needle is used with a powered driver in accordance with teachings of the present disclosure. For some applications, a helical groove 117 may be formed within longitudinal bore 118 proximate opening 116. Helical groove 117 may assist with retaining a biopsy specimen or a bone marrow specimen within longitudinal bore 118. For example, a single thread may be disposed within the longitudinal bore or lumen of the cannula such that the helical groove 117 is defined between turns of the thread. Various techniques and procedures may be satisfactorily used to place the single thread or otherwise form the helical groove, as described WO 2008/033874.

As shown in FIG. 1C, a biopsy needle set 100g may include cannula or outer penetrator 110g with stylet or inner penetrator 120g slidably disposed therein. The proximal ends of cannula 110g and stylet 120g may be similar to those of cannula 110a and stylet 120 depicted in FIG. 1A (e.g., may include hubs 140a and 150a, respectively). For some applications first end 101 of biopsy needle set 100g may minimize damage to skin and soft body tissue at an insertion site. For some applications inner penetrator or stylet 120g may include first end 121 having a plurality of cutting surfaces 125 and 126 formed on exterior portions thereof extending from associated tip 123 towards second end of stylet or inner penetrator 120g. For some applications one or more cutting surfaces 125 may be formed having length 127 extending from tip 123 to associated cutting surfaces 114g in associated cannula 110g. One or more cutting surfaces 126 may be formed adjacent to each cutting surface 125 with second length 128. First length 127 may be greater than second length 128. As shown, lengths 127 and 128 are measured parallel to the central longitudinal axis of stylet 120g. The ratio of first length 127 and second length 128 may be varied in accordance with teachings of the present disclosure to provide optimum performance for penetrating a selected bone and associated bone marrow. Additional details of some embodiments of first end 101 are described in WO 2008/033874.

Figure 2:
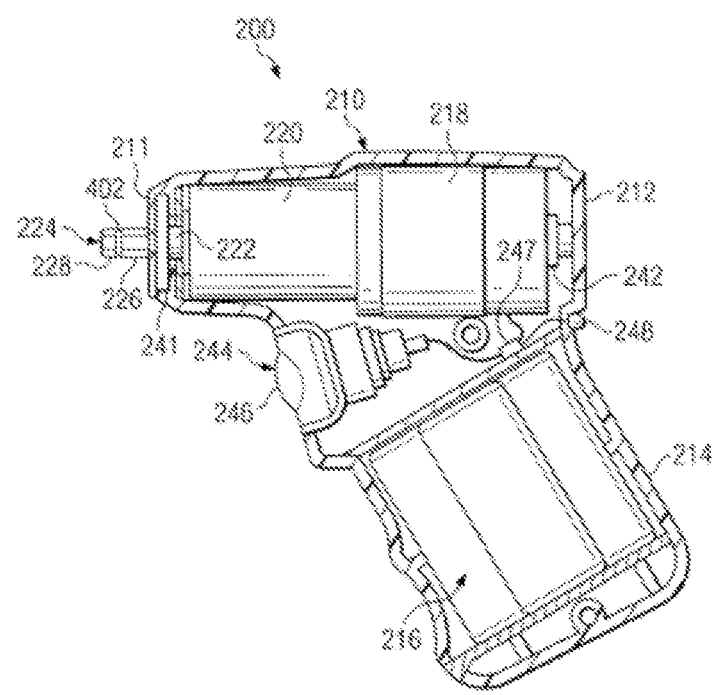
FIG. 2 depicts a cross-sectional side view of one embodiment of the present drivers.

FIG. 2 depicts a cross-sectional view of one embodiment of a driver that can be used with embodiments of the present drivers and kits. In the embodiment shown, powered driver 200 may be used to insert an intraosseous devices into a bone and associated bone marrow. Powered driver 200 may include housing 210 having a general configuration similar to a small pistol defined in part by handle 214. Various components associated with powered driver 200 may be disposed within housing 210 (e.g., handle 214). For example a power source such as battery pack 216 may be disposed within handle 214. Housing 210 may be formed from relatively strong, heavy duty polymeric materials such as polycarbonate or other satisfactory materials. For some applications housing 210 may be formed in two halves (not expressly shown) which may be joined together with a fluid tight seal to protect various components of powered driver 200 disposed therein.

Motor 218 and gear assembly 220 may be disposed within portions of housing 210 adjacent to handle 214. Motor 218 and gear assembly 220 may be generally aligned with each other. Motor 218 may be rotatably engaged with one end of gear assembly 220. Drive shaft 222 may be rotatably engaged with and extend from another end of gear assembly 220 opposite from motor 218. For some applications both motor 218 and gear assembly 220 may have generally cylindrical configurations. Distal end or first end 211 of housing 210 may include an opening with portions of drive shaft 222 extending through the opening, as shown. For some applications, end 224 or the portion of drive shaft 222 extending from first end 211 of housing 210 may have a generally hexagonal cross section with surfaces 226 disposed thereon. Receptacle 263 disposed in second end 252 of coupler assembly 250 may have a matching generally hexagonal cross section, as shown in FIGS. 6A-6C.

Surfaces 226 may extend generally parallel with each other and parallel with respect to a longitudinal axis or rotational axis of drive shaft 222. One or more tapered surfaces 228 may also be formed on end 224 to assist with releasably engaging powered driver 200 with coupler assembly 250. Embodiments of powered driver 200 include speed reduction ratios, for example, of between 60:1 and 80:1, resulting in drive shaft RPMs that are reduced relative to motor RPMs. Coupler assemblies having corresponding openings or receptacles may be releasably engaged with end 224 extending from first end 211 of powered driver 200. For example, end 224 extending from first end 211 of housing 210 may be releasably engaged with receptacle 264 disposed proximate second end 252 of coupler assembly 250, as shown in FIGS. 6A-6B.

For some applications thrust bearing 241 may be disposed between first end or distal end 211 of housing 210 and adjacent portions of gear assembly 220. Thrust bearing 242 may be disposed between second end or proximal end 212 of housing 210 and adjacent portions of motor 218. Thrust bearings 241 and 242 may limit longitudinal movement of motor 218, gear assembly 220 and drive shaft 222 within associated portions of housing 210. Trigger assembly 244 may also be disposed within housing 210 proximate handle 214. Trigger assembly 244 may include trigger or contact switch 246. Motor 218 may be energized and deenergized by alternately depressing and releasing trigger 246. Electrical circuit board 247 may also be disposed within housing 210. Electrical circuit board 247 may be electrically coupled with trigger assembly 244, motor 218, power supply 216 and indicator light 248. For some applications indicator light 248 may be a light emitting diode (LED) or a small more conventional light bulb. For some applications indicator light 248 may be activated when ninety percent (90%) of electrical storage capacity of battery pack 216 has been used. The configuration and dimensions of an intraosseous device formed in accordance with teachings of the present disclosure may vary depending upon respective intended applications for each intraosseous device. For example the length of a biopsy needle formed in accordance with teachings of the present disclosure may vary from approximately five (5) millimeters to thirty (30) millimeters.

Coupler assemblies incorporating teachings of the present disclosure may function as "quick release mechanisms" operable to engage and disengage an IO device from a powered driver (e.g., a driver disposed within a flexible containment bag or sterile sleeve). Such coupler assemblies may allow rotation of an IO device (e.g., biopsy needle or needle set) without damage to the flexible containment bag or sterile sleeve. One end of the coupler assembly may be operable to form a fluid seal or fluid barrier with adjacent portions of the containment bag or sterile sleeve. A coupler assembly incorporating teachings of the present disclosure may also be described as a port assembly attached to a containment bag. Such port assemblies may allow easy engagement or disengagement of a powered driver from an IO device and at the same time allow the powered driver to "power in and power out" an IO device from an insertion site.

Figure 3:
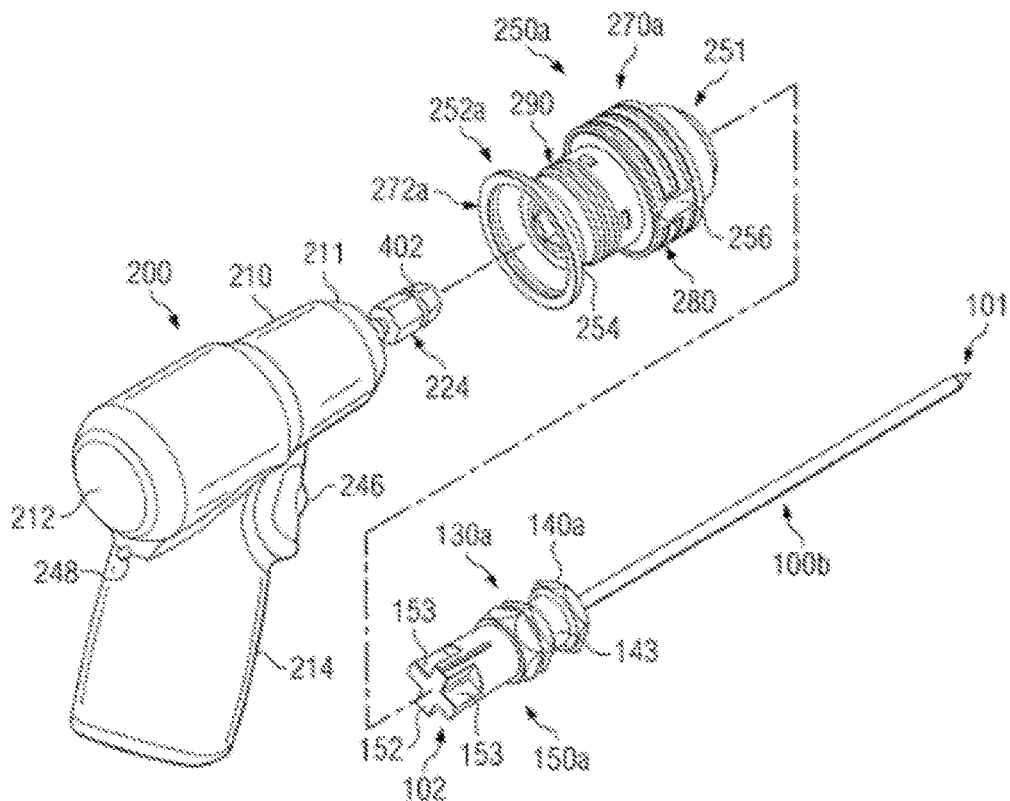
FIG. 3 depicts a perspective view of the driver of FIG. 2 with a corresponding coupler assembly and a third embodiment of the present IO devices.
Figure 4:
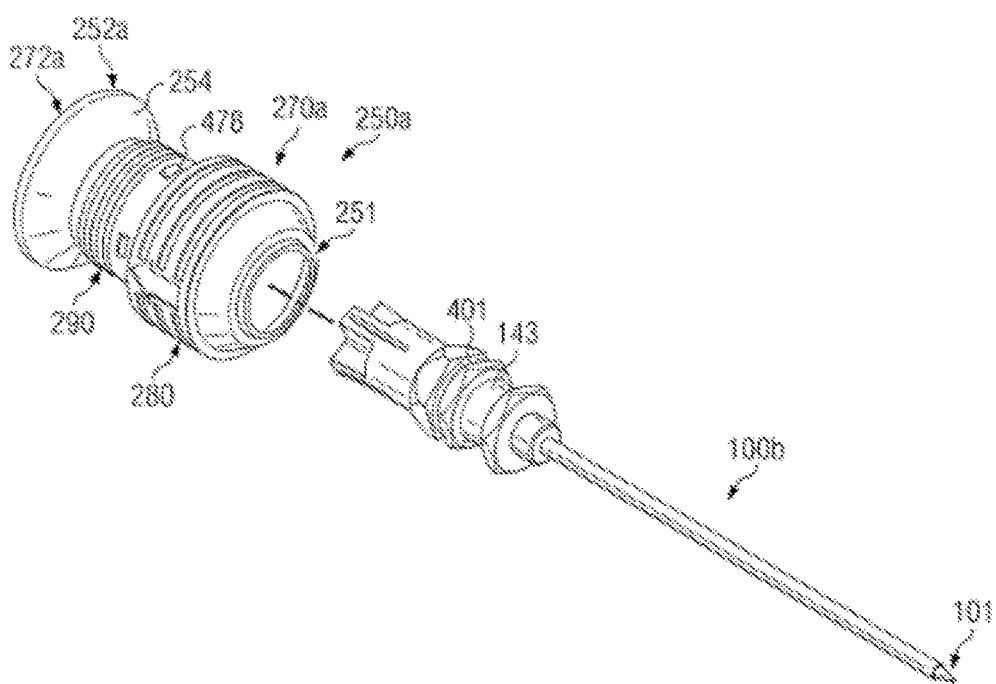
FIG. 4 depicts the coupler assembly and IO device of FIG. 3.
Figure 5:
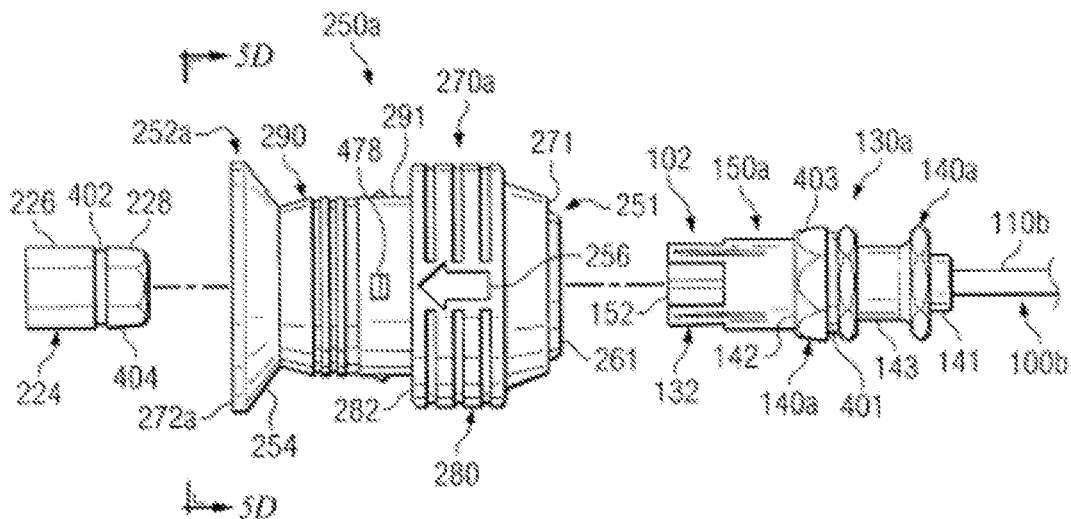
FIG. 5 depicts portions of the driver, coupler assembly, and IO device of FIG. 3.

FIGS. 3-6C depict an example of a coupler assembly 250 suitable for some embodiments of the present assemblies and kits. FIGS. 3-5 are perspective views showing various views of powered driver 200, coupler assembly 250a, and intraosseous device 100b that is substantially similar to device 100a with the exception that device 100b does not include markings 104. Coupler assembly 250a includes a first end 251 operable to be releasably engaged with one end of an intraosseous device such as, but not limited to, second end 102 of biopsy needle set 100b. Coupler assembly 250a also includes a second end 252 operable to be releasably engaged with a portion of a drive shaft extending from a powered driver, such as, but not limited to, end 224 of drive shaft 222 extending from first end 211 of housing 210 of powered driver 200. Though not depicted here, second end 252 of coupler assembly 250 may be securely engaged with an opening in a containment bag or sterile sleeve, as described in WO 2008/033874.

Coupler assemblies incorporating various teachings of the present disclosure may be placed in a medical procedure tray or kit with one end down and an opposite end looking up to allow "hands free" releasable engagement with a powered driver or a manual driver. For example, coupler assembly 250a may be disposed in medical procedure tray with first end 251 facing downward and second end 252 facing up such that end 224 of drive shaft 222 (of driver 200) may be inserted into and releasably engaged with second end 252 of coupler assembly 250 without requiring an operator or user to physically contact or manipulate any portion of coupler assembly 250a. As described below, coupler 250a may include a "hands free" latching mechanism.

In the embodiment shown, coupler assembly 250a may include elongated core 260 with housing assembly 270 slidably disposed on exterior portions of elongated core 260. Housing assembly 270/270a may include first end 271 and second end 272 which may be generally aligned with respective first end 261 and respective second end 262 of elongated core 260. For some applications, elongated core 260 may have a generally cylindrical configuration defined in first exterior portion 260a and second exterior portion 260b with various shoulders and/or recesses formed thereon. For some embodiments first exterior portion 260a may have a larger diameter than second exterior portion 260b. Housing assembly 270 may be described as having a generally hollow, cylindrical configuration defined in part by first housing segment 280 and second housing segment 290. The first end of housing segment 280 may generally correspond with first end 271 of housing assembly 270. The second end of second housing segment 290 may generally correspond with second end 272 of housing assembly 270. First end 291 of second housing segment 290 may be described as having a generally cylindrical configuration with an outside diameter smaller than the adjacent inside diameter of second end 282 of first housing segment 280. Second housing segment 290 may slide longitudinally from a first position (FIG. 6A) to a second position (FIG. 6B) within second end 282 of first housing segment 280 to release one end of a drive shaft engaged with second end 252 of coupler assembly 250.

A biasing mechanism such as coiled spring 274 may be disposed around exterior portion 260a of generally elongated core 260. First end 275 of coiled spring 274 may contact annular shoulder 284 formed on interior portions of first housing segment 280. Second end 276 of coiled spring 274 may contact annular shoulder 278 disposed proximate first end 291 of second housing segment 290. Coil spring 274, annular shoulder 284 and annular shoulder 278 may cooperate with each other to generally maintain first housing segment 280 and second housing segment 290 in a first extended position relative to each other. Other biasing mechanisms such as, but not limited to, leaf springs and bellows (not expressly shown) may also be disposed between annular shoulder 284 and annular shoulder 278. Annular shoulder 278, associated with second end 276 of coiled spring 274, may extend radially outward from generally cylindrical ring 277. Generally cylindrical ring 277 may be slidably and rotatably disposed on exterior portion 260a of elongated core 260. Annular shoulder 279 may be disposed on interior portions of generally cylindrical ring 277 and may extend radially inward toward adjacent portions of elongated core 260. Annular shoulder 268 may be formed on exterior portion 260a of elongated core 260 intermediate first end 261 and second end 262. The configuration and dimensions of annular shoulder 268 and annular shoulder 279 are selected to be compatible with each other such that engagement between annular shoulder 279 of generally cylindrical ring 277 with annular shoulder 268 of elongated core 260 may limit movement of second housing segment 290 longitudinally in the direction of second end 262 of elongated core 260.

For some applications a plurality of flexible collets or fingers 477 may extend from generally cylindrical ring 277 opposite from annular shoulder 278. Respective collet heads 478 may be formed on the end of each collet 477 opposite from annular shoulder 278. The dimensions and configuration of collet heads 478 may be selected to be received within respective slots or openings 297 formed in second housing 290. During manufacture of coupler assembly 250a, each collet head 478 may be disposed within respective slot or opening 297 to securely engage generally cylindrical ring 277 and annular shoulder 278 proximate first end 291 of second housing segment 290. As a result, second housing segment 290 and annular shoulder 278 may generally move as a single unit relative to elongated core 260 and first housing segment 280. During disengagement of an intraosseous device from first end 251 of coupler assembly 250a, first housing segment 280 may move or slide longitudinally toward second housing segment 290. In a similar manner, second housing segment 290 may move or slide longitudinally toward first housing segment 280 during disengagement of a powered driver from second end 252 of coupler assembly 250a.

Annular shoulder 267 may be formed on exterior portions of elongated core 260 proximate first end 261. Annular shoulder 267 may engage portions of first end 271 of housing 270 to limit longitudinal movement of first housing segment 280 during longitudinal movement of second housing segment 290 towards first end 261 of elongated core 260 during disengagement of a powered driver from second end 252 of coupler assembly 250a. As previously noted, annular shoulder 268 may be formed on exterior portions of elongated core 260 between first end 261 and second end 262. Engagement between annular shoulder 268 and annular shoulder 279 of generally cylindrical ring 277 may limit movement of second housing segment 290 toward second end 262 of elongated core 260. Contact between spring 274 and annular shoulder 278 and annular shoulder 284 of first housing segment 280 may limit the longitudinal movement of first housing segment 280 in the direction of second end 262 of elongated core 260 during disengagement of an intraosseous device from first end 251 of coupler assembly 250a.

Generally cylindrical ring 277 and attached annular shoulder 279 may slide longitudinally on exterior portions of annular core 260 between annual shoulder 268 and annular shoulder 267. First housing segment 280 may move longitudinally toward second end 262 of elongated core 260 to release one end of intraosseous device from engagement with first end 251 of coupler assembly 250a. In a similar manner, second housing segment 290 may move longitudinally toward first end 261 of elongated core 260 to release one end of a drive shaft extending from a powered driver engaged with second end 252 of coupler assembly 250a. A wide variety of latches and latch mechanisms may be satisfactorily used to releasably engage one end of an intraosseous device within a first end of a coupler assembly incorporating teachings of the present disclosure. In a similar manner, a wide variety of latches and latch mechanisms may be satisfactorily used to releasably engage one end of a drive shaft extending from a powered driver or manual driver within a second end of the coupler assembly incorporating teachings of the present disclosure.

For embodiments represented by coupler assembly 250a, first latch 410 may be disposed on exterior portions of elongated core 260 proximate receptacle 263 adjacent to first end 261 to releasably engage one end of an IO device such as second end 102 of biopsy needle set 100b within receptacle 263 of coupler assembly 250a. Second latch mechanism 420 may be disposed on exterior portions of elongated core 260 proximate receptacle 264 adjacent to second end 262 to releasably engage one end of a drive shaft with second end 252 of coupler assembly 250a. Second latch 420 may be used to releasably engage one portion of a drive shaft such as end 224 of drive shaft 222 extending from powered driver 200 within second end 252 of coupler assembly 250a. Latch 410 may releasably engage an intraosseous device with first end 251 of coupler assembly 250a and substantially the same latch 420 may releasably engage a powered driver with second end 252 of coupler assembly 250a.

For some applications, latches 410 and 420 may have similar configurations such as a general "omega" shape (e.g., latch 420). However, latch 410 may have larger dimensions corresponding generally with exterior portion 260a of elongated core 260. Latch 420 may have smaller dimensions corresponding generally with exterior portion 260b of elongated core 260. Various features of the present disclosure may be described with respect to latch mechanism 420 along with adjacent portions of second housing segment 290 and exterior portion 260b of elongated core 260. Respective detents 421 and 422 may be formed on opposite ends of generally omega shaped latch 420. In a similar manner, respective detents (not expressly shown) may be formed on the ends of generally omega shaped latch 410. The configuration and dimensions of detents 421 and 422 may be compatible with placing each detent 421 and 422 in a respective slot or opening extending between exterior portion 260b of elongated core 260 to interior portions of receptacle 264 disposed proximate second end 252 of coupler assembly 250a. Latch 420 may have a first position in which portions of detents 421 and 422 may extend through the respective slots. The dimensions and configuration of detent 421 and 422 may be operable to be securely engaged with annular groove 402 formed in end 224 of powered driver 200. In a similar manner, respective detents on associated latch 410 may be releasably engaged with annular groove 401 disposed in second end 102 of biopsy needle 100b. For some applications, a plurality of tapered surfaces 403 may be formed on exterior portions of hub 140a proximate first end 142 to radially expand detent mechanisms associated with omega shaped latch 410 radially outward while inserting second end 102 of biopsy needle 100b into first end 251 of coupler assembly 250a. The detent mechanism may "snap" into annular groove 401 when aligned therewith. In a similar manner, a plurality of tapered surfaces 228 may be formed on exterior portions of end 224 of drive shaft 222 extending from powered driver 200 to radially expand detent mechanisms 421 and 422 radially outward during the insertion of end 224 of powered driver 200 into second end 252 of coupler assembly 250a.

Detent mechanisms 421 and 422 will "snap" into annular groove 402 when aligned therewith.

Engagement between detent mechanisms associated with latch 410 with annular groove 401 of hub assembly 130a will generally retain second end 102 of biopsy needle 100b securely engaged with first end 251 of coupler assembly 250a. This engagement may allow powered driver 200 to rotate or spin cannula or biopsy needle 110b while withdrawing cannula or biopsy needle 110b from an insertion site. In a similar manner, engagement between detent mechanisms 421 and 422 of omega shaped latch 420 and annular groove 402 of end 224 of powered driver 200 will generally retain second end 252 of coupler assembly 250a engaged with powered driver 100 during withdrawal of cannula 110b from an insertion site.

Biopsy needle set 100b may be released from first end 251 of coupler assembly 250a by sliding first housing segment 280 longitudinally toward second end 262 of elongated core 260. Such movement of first housing segment 280 will result in interior tapered surface 286 contacting exterior portions of omega shaped latch 410 and compressing omega shaped latch 410 to radially expand associated detent mechanisms (not expressly shown) from engagement with annular groove 401 of hub assembly 130a. As a result, biopsy needle set 100b may be easily withdrawn from first end 251 of coupler assembly 250a. In a similar manner, longitudinal movement of second housing segment 290 toward first end 251 of coupler assembly 250a will result in interior tapered surface 296 contacting exterior portions of omega shaped latch 420 to compress generally omega shaped latch 420 and withdraw or retract detent mechanisms 421 and 422 from engagement with annular groove 402 of end 224. As a result, powered driver 200 and second end 222 of coupler assembly 250a may be easily disconnected from each other.

Flange 254 may be generally described as having an enlarged funnel shaped or bell shaped configuration. The dimensions and configuration of flange 254 may be selected to be compatible with end 211 of powered driver 200. As previously noted, coupler assembly 250a may be securely engaged with an opening formed in a containment bag or sterile sleeve in accordance with teachings of the present disclosure. For embodiments such as the one shown, end 272 of housing 270 of coupler assembly 250a may include annular ring 370 operable to be securely engaged with adjacent portions of flange 254. The outside diameter of annular ring 370 may generally correspond with the outside diameter of adjacent portions of flange 254. The inside diameter of annular ring 370 may also generally correspond with the inside diameter of adjacent portions of flange 254. For some embodiments a plurality of posts 372 and generally V shaped grooves 374 may be alternatingly disposed on the extreme end of flange 254. Annular ring 370 may include a plurality of holes 371 sized to received respective posts 372 therein. Annular ring 370 may also include a plurality of generally V shaped projections 376 sized to be received within respective generally V shaped grooves 374 formed in adjacent portions of flange 254. For embodiments such as the one shown, portions of a containment bag (e.g., around an opening) may be disposed between annular ring 370 and adjacent portions of flange 254. For example, post 372 may be inserted through a corresponding hole in a containment bag adjacent to the perimeter of an opening in the containment bag. Holes 371 in annular ring 370 may be aligned with respective posts 372. Other portions of a containment bag (e.g., adjacent to an opening) may be trapped between respective V shaped projections 376 and V shaped grooves 374. Various welding techniques including, but not limited to, laser welding may be applied to posts 372 to bond annular ring 370 with adjacent portions of flange 354. As a result, a perimeter of a containment bag around an opening in the containment bag may be securely engaged with second end 252 of coupler assembly 250a.

Figure 7A:
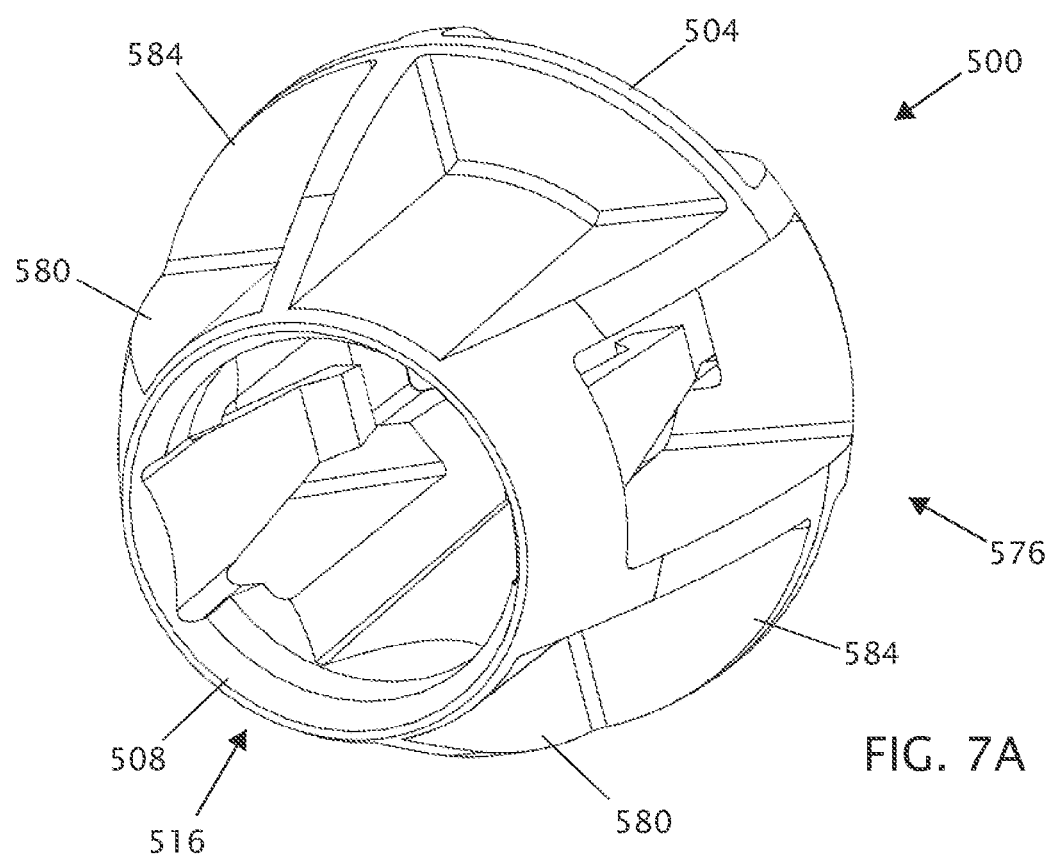
FIGS. 7A-7H depict various views of one embodiment of the present snap handles for use with the present IO devices.
Figure 7B:
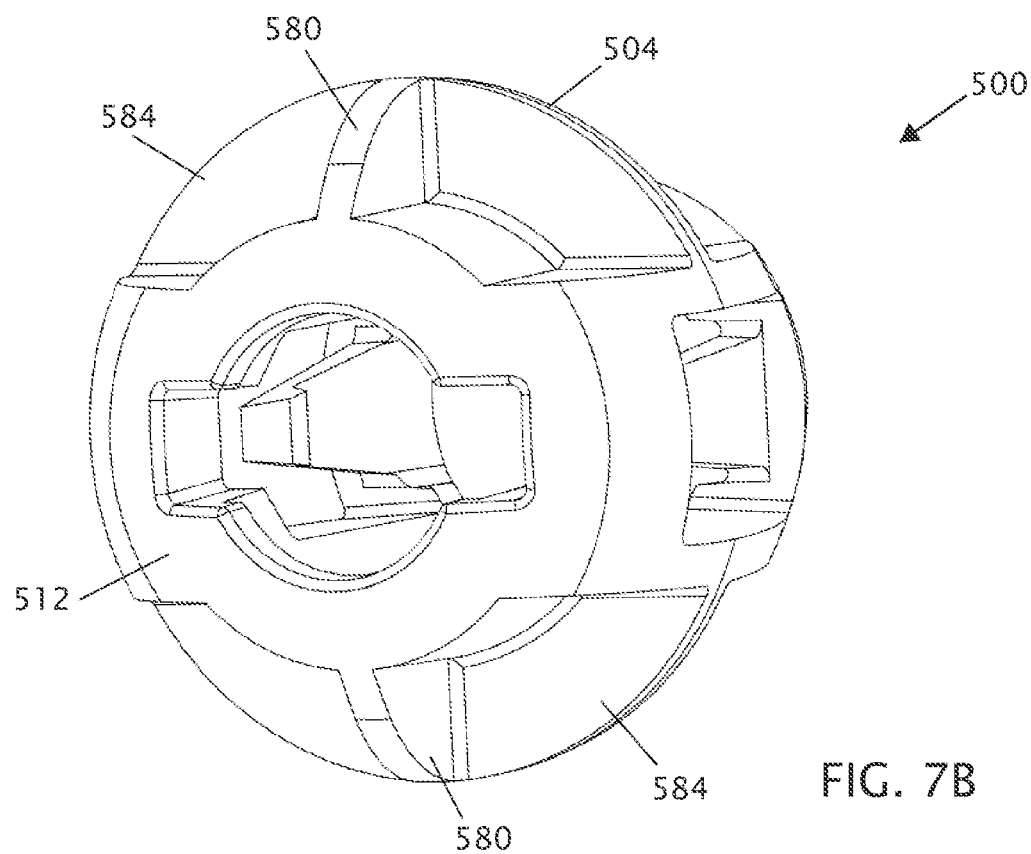
Figure 7C:
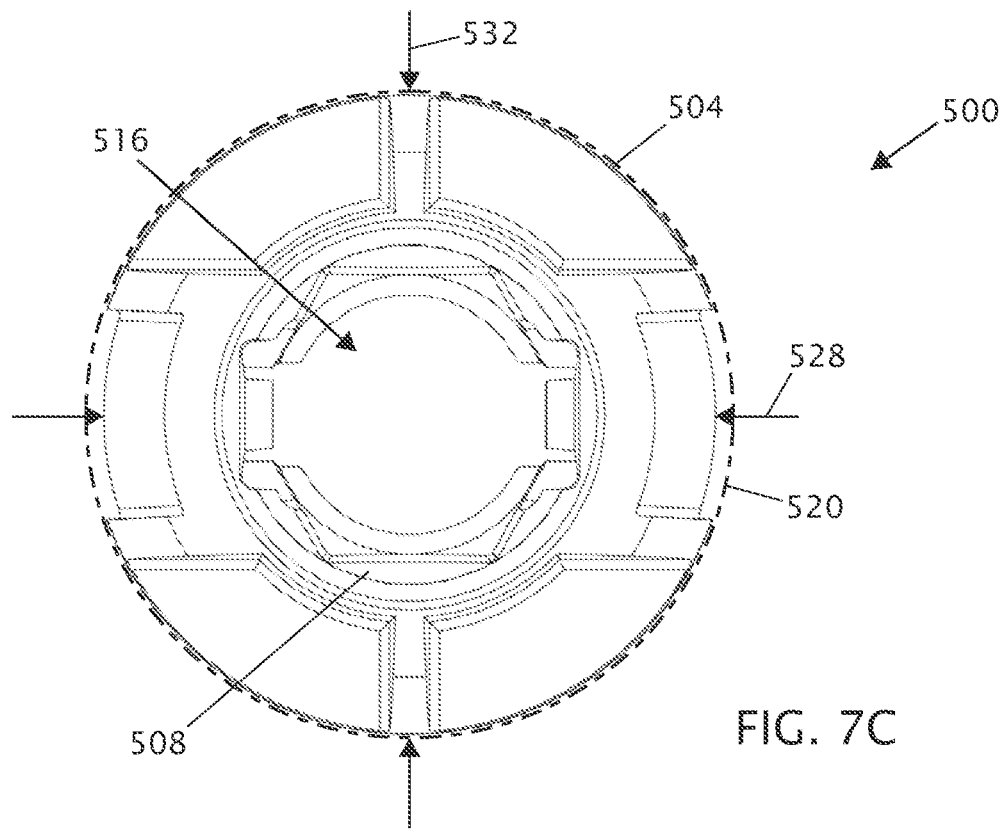
Figure 7D:
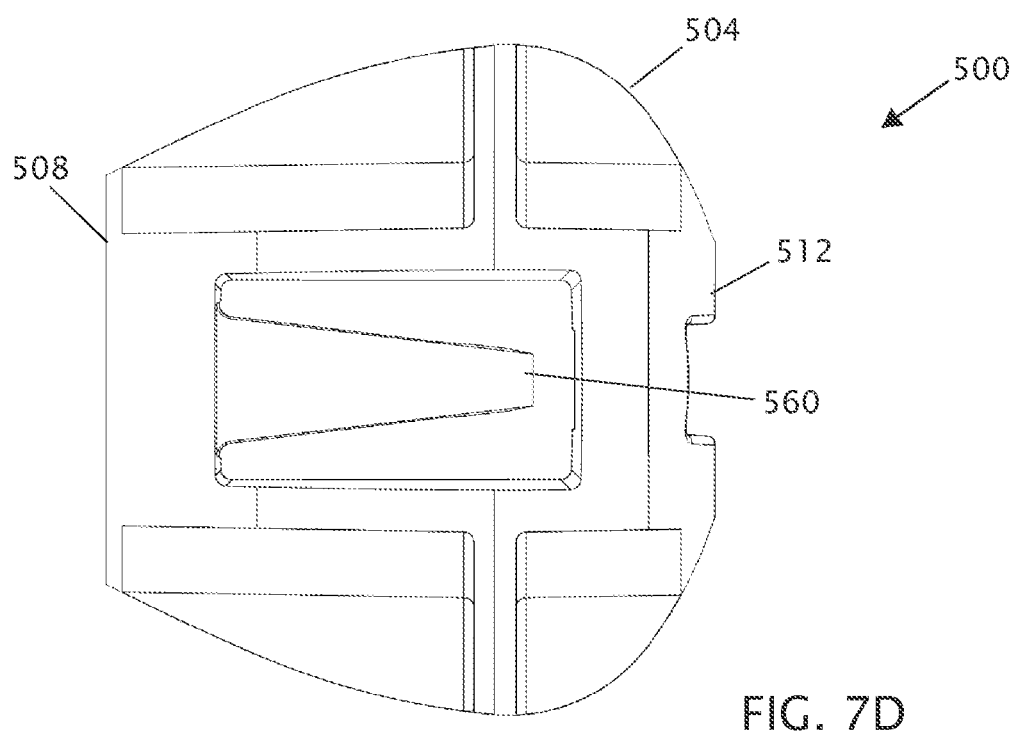
Figure 7E:
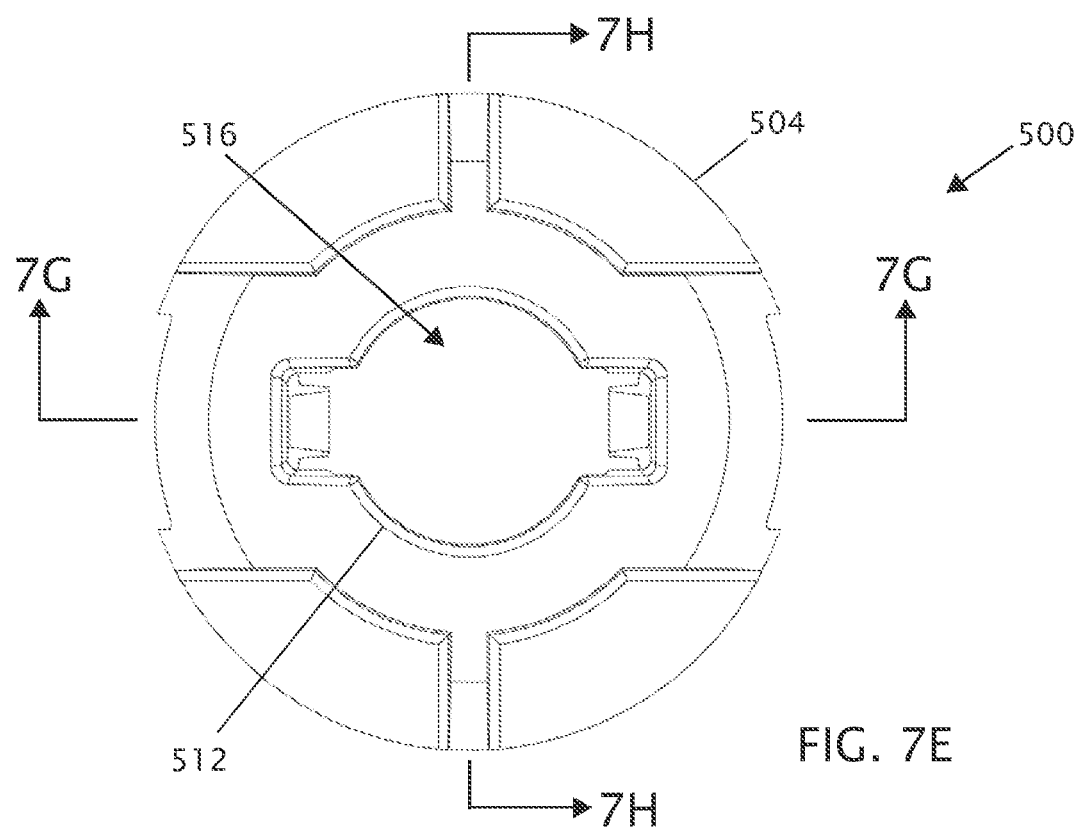
Figure 7F:
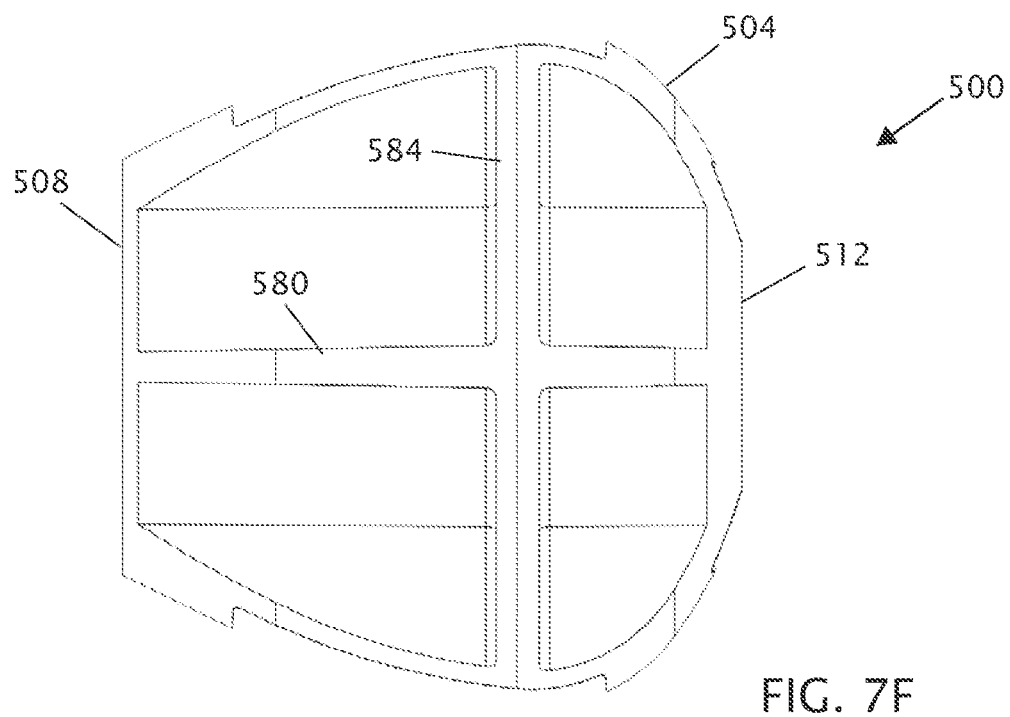
Figure 7G:
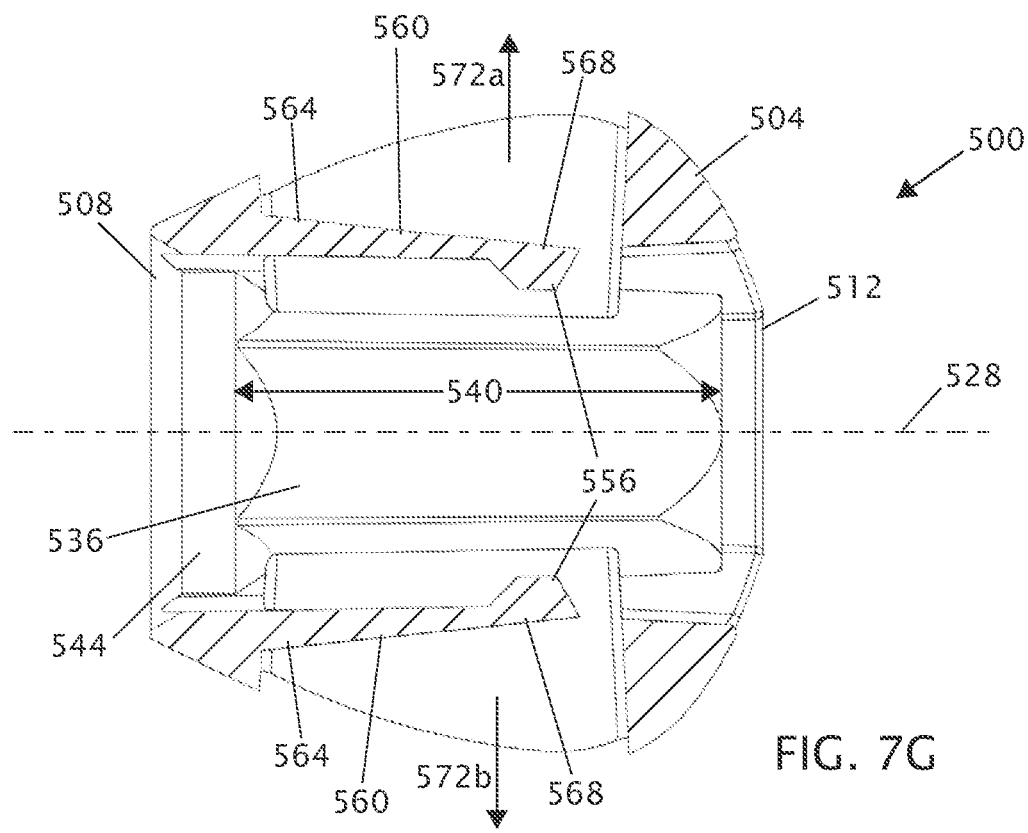
Figure 7H:
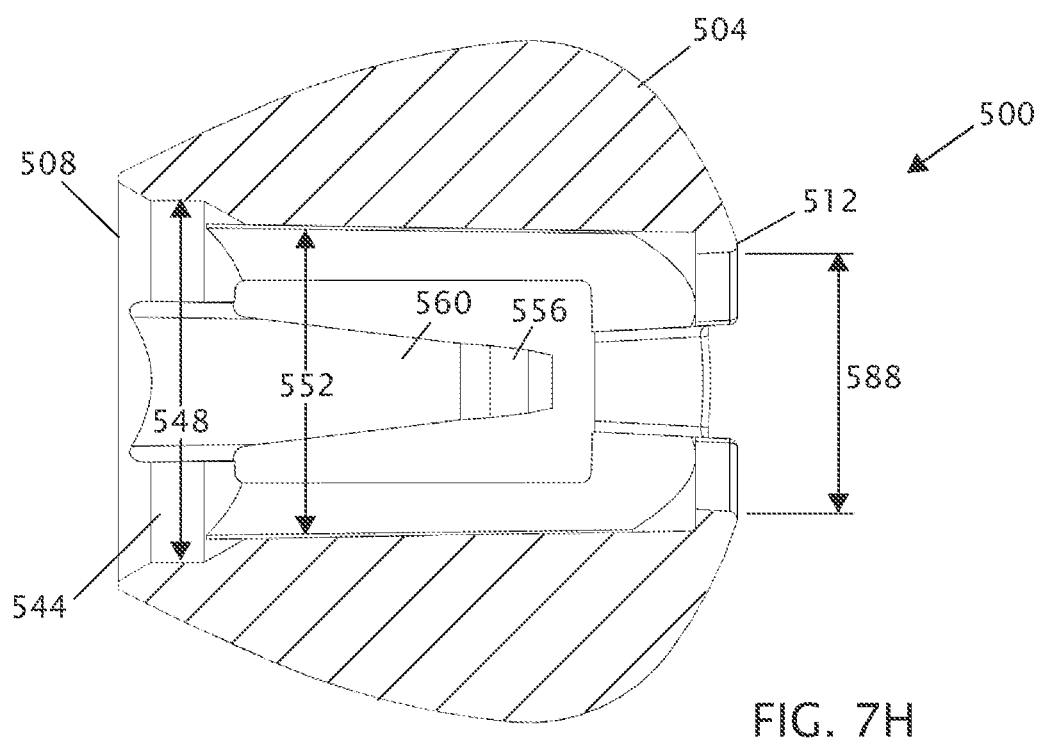

FIGS. 7A-7H depict various views of one embodiment 500 of the present handles or "snap" handles, at least some of which are configured to "snap" onto a hub of an IO device to facilitate hand manipulation of the IO device by a user. FIGS. 7A and 7B depict front and rear perspective views of handle 500; FIG. 7C depicts a front view of handle 500; FIG. 7D depicts a left side view of handle 500: FIG. 7E depicts a rear view of handle 500: FIG. 7F depict a top view of handle 500; FIG. 7G depicts a top cross-sectional view of handle 500 taken along the line 7G-7G of FIG. 7E; and FIG. 7H depicts a side cross-sectional view of handle 500 taken along the line 7H-7H of FIG. 7E. In the embodiment shown, handle 500 includes a body 504 having a first or distal end 508, a second or proximal end 512, and a passage 516 extending from first end 508 to second end 512. Body 504 can comprise, for example, a polymer and/or may be molded or machined by known manufacturing methods. In some embodiments, such as the one shown, body 504 has a cross-sectional (outer) perimeter 520 (FIG. 7C) that is substantially circular. For example, perimeter 520 has a first transverse dimension 524 that is perpendicular to a longitudinal axis 528 of passage 520, and a second transverse dimension 532 that is perpendicular to first transverse dimension 524. Second transverse dimension 532 may be nearly equal to or within a given percentage of first transverse dimension. For example, in some embodiment (such as the one shown), (the value of) first transverse dimension 524 does not vary from (the value of) second transverse dimension 532 by more than ten percent of (the value of) first transverse dimension 524.

In the embodiment shown, passage 516 includes a portion 536 (e.g., having a length 540) between distal end 508 and proximal end 512 that includes a non-circular cross-sectional shape. The non-circular cross-sectional shape allows handle 500 to receive a hub (e.g., hub 140c and/or 140d) of an IO device having a similar non-circular cross-sectional shape in a non-rotational fashion (i.e., such that the hub is not permitted to rotated relative to the handle). In this embodiment, portion 536 has a hexagonal cross-sectional shape. In some embodiments, portion 536 extends from distal end 508 toward proximal end 512. In the embodiments shown, however, passage 516 include an entry portion 544 disposed between distal end 508 and portion 536. In this embodiment, entry portion 544 has a circular cross-sectional shape having a diameter 548 that is equal to or larger than a maximum transverse dimension of portion 536 of the passage, and that is larger than a corresponding minimum transverse dimension 552 of portion 536 (and a cross-sectional area that is greater than a cross-sectional area of portion 536.

In some embodiments, handle 500 includes one or more projections 556 extending inward toward axis 528 to resist removal of a hub (e.g., hub 140c and/or 140d) of an IO device if the hub is disposed in the passage. For example, in the embodiment shown, handle 500 includes one or more (e.g., two, as shown) resilient arms 560, each having a first end 564 coupled in fixed relation to (e.g., unitary with, as shown) body 504, and a second end 568 extending from first 564 end such that second end 568 is movable toward rotational axis 528 of the handle. In this embodiment, protrusions 556 are each coupled to a different one of second ends 568 of arms 560, and arms 560 are each configured to be deflected away from rotation axis 528 (in directions 572a and 572b, respectively) to permit insertion and removal of a hub (e.g., hub 140c and/or hub 140d). In this embodiment, first end 564 of each arm 560 is closer to distal end 508 than to proximal end 512, and the length of each arm 560 is substantially parallel to axis 528 such that second end 568 of each arm 560 and the respective projection (556) is closer to proximal end 512 than to distal end 508. In this embodiment, projections 556 are tapered to permit a user to press a hub of an IO device into passage 516 such that the hub itself will deflect second ends 568 of the arms outward relative to axis 528 to permit the hub to be inserted, and, once a groove or detent (e.g., groove 612c or groove 612d) of the hub becomes aligned with projections 556, second ends 568 will resiliently flex back toward axis 528 to insert projections 528 into the groove on the hub. Similarly, while projections 556 will resist removal of the hub from passage 516, projections 556 are tapered to permit a user to remove the hub from passage 516 without first flexing second ends 568 of arms 560 outward relative to axis. Stated another way, although projections 556 will resist removal of the hub from passage 516, a user can pull the IO device away from handle 500 and the hub itself will cause second ends 568 of the arms to flex outward relative to axis 528 to permit the hub to withdraw from passage 516.

In the embodiment shown, exterior portions of body 504 includes a plurality of ribs 576 configured to facilitate a user's ability to grasp handle 500, and thereby increase the amount of torque that a user can exert on handle 500. In this embodiment, ribs 576 include a plurality of longitudinal ribs 580 extending parallel to rotational axis 528 of handle 500, and at least one circumferential rib 584 extending between longitudinal ribs 580. In this embodiment, each of ribs 576 has a distal edge and the distal edges of at least three of the ribs lies on a circle (e.g., perimeter 520) circumscribing the handle (see FIG. 7C). In the embodiment shown, body 504 includes an opening or portion of passage 516 extending through second end 512 that has at least one transverse dimension 588 that is smaller than a corresponding transverse dimension 552 of passage 516.

FIGS. 8A and 8B depict another embodiment 100c of the present an IO devices or needle sets. Needle set 100c is similar in several respects to IO needle set 100a. As with needle set 100a, needle set 100c comprises a hollow outer penetrator or cannula 110c, a corresponding inner penetrator or stylet (or trocar) 120, and a hub assembly 130c. In the embodiment shown, first end 111c of cannula 110c and first end 121 of stylet 120 are operable or configured to penetrate a bone and associated bone marrow. Various features of first end 111c of cannula 110c are shown in more detail in FIGS. 12A-12C. First end 101 of IO needle set 100a corresponds generally with first end 111a of cannula 110a and first end 121 of stylet 120. In some embodiments, cannula 110c may have a length 600 of between sixty (60) and two hundred-fifty (250) millimeters (e.g., equal to any one of, or between any two of: 60, 75, 100, 125, 150, 175, 200, 225, and/or 250 millimeters) and/or a nominal outside diameter corresponding to that of a ten (10) or an eleven (11) gauge needle).

Hub assembly 130c is similar to hub assembly 130a. For example, hub assembly 130c may be configured and/or used to releasably dispose stylet 120 within the longitudinal bore or lumen of cannula 110c. In the embodiment shown, hub assembly 130c includes a first hub 140c and a second hub 150c and has an overall length 604 of between twenty five (25) and thirty five (35) millimeters (e.g., thirty one (31) millimeters). A second end of cannula 110c, opposite from first end 111c, may be securely engaged with hub 140c. The second end of stylet 120, opposite from first end 121, may be securely engaged with hub 150c and extending from first end 151 of hub 150c. As shown in FIGS. 8A-8B, cannula 110c may extend longitudinally from first end 141 of hub 140c. Stylet 120 may also extend from the first end of hub 150c.

A second end 142 (FIG. 11) of hub 140c may include a standard Luer lock fitting which may be releasably engaged with a corresponding Luer lock fitting disposed within the first end of second hub 150c. The Luer lock fitting disposed on the second end of hub 140c may be in fluid communication with the bore or passage in cannula 110c, and may be operable to be releasably engaged with a standard syringe type fitting and/or a standard intravenous (IV) connection. Hub 140c may include second end 142 with opening 144 formed therein. A passageway may extend from second end 142 towards first end 141 of hub 140d, as shown. A passageway may be operable to communicate fluids with lumen 118 of cannula 100c. Second end 142 of hub 140c may include various features of a conventional Luer lock connection or fitting, including threads (e.g., similar to threads 148 in FIG. 1A), and corresponding threads (e.g., similar to threads 158 in FIG. 1A) may be formed within first end 151 of hub 150a.

In the embodiment shown, hub 150c includes second end 152 that generally corresponds with second end 132 of hub assembly 130c and second end 102 of IO needle set 100c. Hub 140c may include first end 141 which may generally correspond with first end 131 of hub assembly 130c. Cannula 110c may extend longitudinally from first end 141 of hub 140c and first end 131 of hub assembly 130c. In the embodiment shown, intraosseous device or aspiration needle set 100c includes first end 151 of hub 150a spaced from second end 142 of hub 140c. Portions of stylet 120 extending from first end 151 of hub 150c are shown slidably disposed within lumen or longitudinal bore 118 of cannula 110c.

In the embodiment shown, the second end of a hub assembly may be operable to be disposed within a receptacle formed in a coupler assembly, as described above with reference to FIGS. 6A-6B. One feature of the present disclosure may include forming a hub assembly which may be releasably engaged within a first receptacle disposed in a first end of a coupler assembly (e.g., receptacle 263 proximate first end 261 of elongated core 260 as shown in FIGS. 6A-6B). The dimensions and configuration of receptacle 263 may be selected to prevent rotation of hub 150c relative to hub 140c if hub assembly 130c is disposed in receptacle 263 (e.g., while inserting (rotating) an IO device into a bone and associated bone marrow). For example, at least one portion 608c of hub assembly 130d may have a generally hexagonal cross section operable to be received within the generally hexagonal cross section of receptacle 263 disposed proximate first end 251 of coupler assembly 250, as shown in FIGS. 6A-6B. Additionally, hub assembly 130c differs from hub assembly 130a in that hub 150c also has a hexagonal cross-sectional shape. In other embodiments, various cross sections other than hexagonal may be satisfactorily used to releasably engage a powered driver with one end of a coupler assembly and an intraosseous device with an opposite end of the coupler assembly. In the embodiment shown, portion 608c is also configured to be received in portion 536 of the passage (516) in handle 500 such that hub 140c is substantially prevented from rotating relative to handle 500 and handle 500 can be rotated to rotate cannula 110c. In this embodiment, hub 140c also includes groove or detent 612c configured (e.g., sized and positioned) to receive projection 556 of handle 500 if hub 140c is inserted far enough into passage 516 of handle 500 for projection 556 to extend into groove 612c, such that projection 556 will resist removal of hub 140c from handle 500.

In the embodiment shown, hub first end 141 of second hub 140c also includes a projection 616 having a circular cross-sectional shape and configured to extend into an end of a tube 620 to retain the tube over the needle set 100c such that the tube extends beyond tip 121 to reduce the likelihood of a user unintentionally poking or puncturing anything with tip 121. Aspiration needle sets may include a trocar, stylet, or penetrator in combination with an associated cannula, catheter or outer penetrator. However, biopsy needles formed in accordance with teachings of the present disclosure may or may not include a trocar, stylet, or inner penetrator. A powered driver may be releasably engaged with a second receptacle disposed in a second end of the coupler assembly (e.g., receptacle 264 proximate second end 262 of elongated core 260 as shown in FIGS. 6A-6B).

FIGS. 9A and 9B depict another embodiment 110d of the present an IO devices or cannulas. Cannula 110d is similar in several respects cannula 110c. For example, various features of first end 111d of cannula 110d are shown in more detail in FIGS. 12A-12C. By way of further example, cannula 110d includes hub 140d that is substantially similar to hub 140c. Cannula 110d primarily differs from cannula 140c in that cannula 110d has a diameter that is sized to fit within cannula 110c and cannula 110d has a length 624 that may be greater than length 600 of cannula 110c. For example, cannula 110d may have a nominal outside diameter corresponding to that of a twelve (12) or a thirteen (13) gauge needle, depending on the size of cannula 110c with which a particular embodiment of cannula 140c is designed to work. In general, cannula 110d may have a diameter that is two gauge sizes smaller than that of cannula 110d (e.g., a thirteen (13) gauge cannula 110d can be expected to fit within an eleven (11) gauge cannula 110c, or a twelve (12) gauge cannula 110d can be expected to fit within a ten (10) gauge cannula 110c). In such embodiments, length 624 of cannula 110d may be greater than length 600 of cannula 110c to permit end 111d of cannula 110d to extend beyond end 111c of cannula 110c, such as, for example, to facilitate the collection of bone marrow samples. In such embodiments, length 624 of cannula 110d may be between eighty (80) and three hundred (300) millimeters (e.g., equal to any one of, or between any two of: 80, 100, 125, 150, 175, 200, 225, 250, 275, and/or 300 millimeters). In this embodiment, length 628 of hub 140d is between twelve (12) and twenty five (25) millimeters (e.g., 17.5 millimeters).

As with hub 140c, hub 140d includes a second end 142 that can include a standard Luer lock fitting. The Luer lock fitting disposed on the second end of hub 140d may be in fluid communication with the bore or passage in cannula 110d, and may be operable to be releasably engaged with a standard syringe type fitting and/or a standard intravenous (IV) connection. Hub 140c may include second end 142 with opening 144 formed therein. A passageway may extend from second end 142 towards first end 141 of hub 140d, as shown. A passageway may be operable to communicate fluids with lumen 118 of cannula 100d. Second end 142 of hub 140d may include various features of a conventional Luer lock connection or fitting, including threads (e.g., similar to threads 148 in FIG. 1A). Cannula 110d may extend longitudinally from first end 141 of hub 140d.

In the embodiment shown, the second end of a hub assembly may be operable to be disposed within a receptacle formed in a coupler assembly, as described above with reference to FIGS. 6A-6B. One feature of the present disclosure may include forming a hub assembly which may be releasably engaged within a first receptacle disposed in a first end of a coupler assembly (e.g., receptacle 263 proximate first end 261 of elongated core 260 as shown in FIGS. 6A-6B). The dimensions and configuration of receptacle 263 may be selected to prevent rotation of hub 140d relative to the receptacle if hub 140c is disposed in receptacle 263 (e.g., while inserting (rotating) an ID device into a bone and associated bone marrow). For example, at least one portion 608d of hub assembly 140d may have a generally hexagonal cross section operable to be received within the generally hexagonal cross section of receptacle 263 disposed proximate first end 251 of coupler assembly 250, as shown in FIGS. 6A-6B. In other embodiments, various cross sections other than hexagonal may be satisfactorily used to releasably engage a powered driver with one end of a coupler assembly and an intraosseous device with an opposite end of the coupler assembly. In the embodiment shown, portion 608d is also configured to be received in portion 536 of the passage (516) in handle 500 such that hub 140d is substantially prevented from rotating relative to handle 500 and handle 500 can be rotated to rotate cannula 110d. In this embodiment, hub 140d also includes groove or detent 612d configured (e.g., sized and positioned) to receive projection 556 of handle 500 if hub 140d is inserted far enough into passage 516 of handle 500 for projection 556 to extend into groove 612d, such that projection 556 will resist removal of hub 140d from handle 500.

In the embodiment shown, hub first end 141 of second hub 140c also includes a projection 616d having a circular cross-sectional shape and configured to extend into an end of a tube 620d to retain the tube over cannula 110d such that the tube extends beyond tip 111d to reduce the likelihood of a user unintentionally poking or puncturing anything with tip 111d. A powered driver may be releasably engaged with a second receptacle disposed in a second end of the coupler assembly (e.g., receptacle 264 proximate second end 262 of elongated core 260 as shown in FIGS. 6A-6B).

Figure 10:
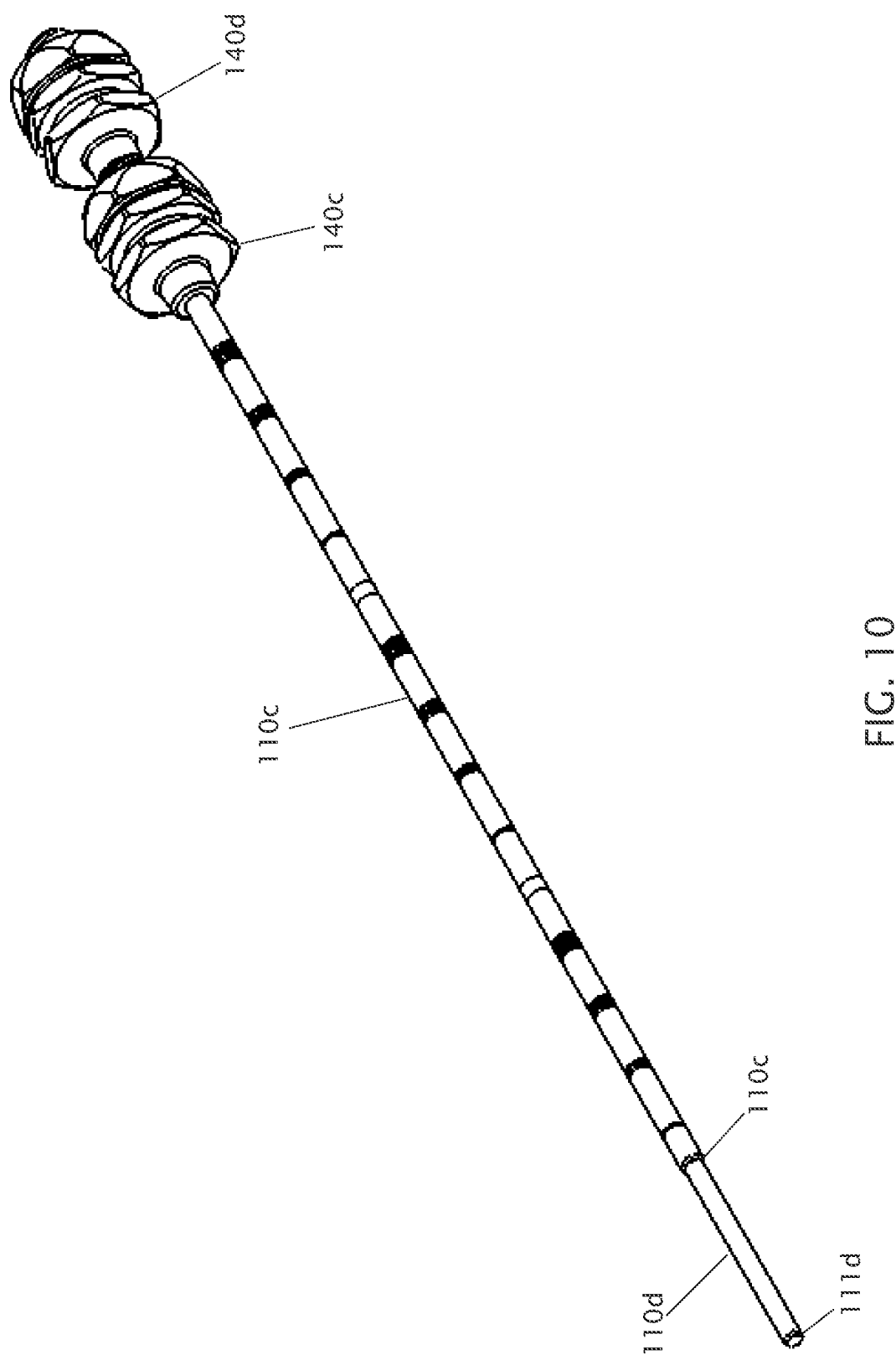
FIGS. 10 and 11 depict perspective and cross-sectional views, respectively, of the cannula of the device of FIGS. 8A and 8B inserted into the cannula of the device of FIGS. 9A and 9B.
Figure 11:
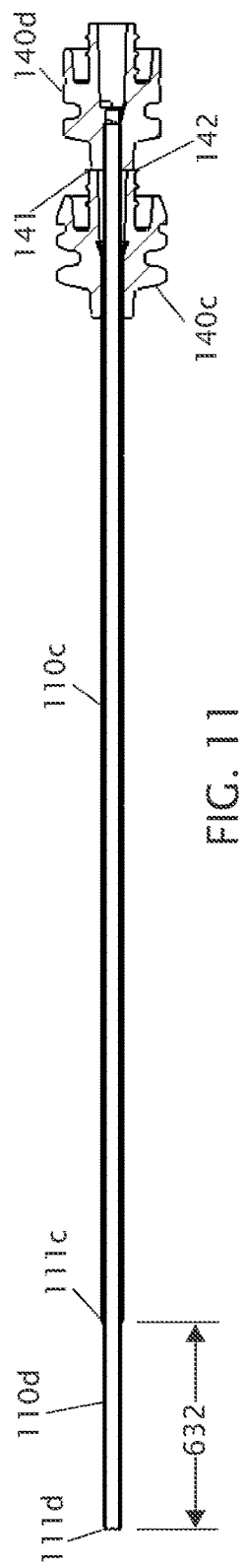

FIGS. 10 and 11 depict cannula 110d disposed in cannula 110c, with first end 141 of hub 140d in contact with second end 142 of hub 140c, and with first end 111d of cannula 110d extending beyond first end 111c of cannula 110c by a distance 632.

Figure 12C:
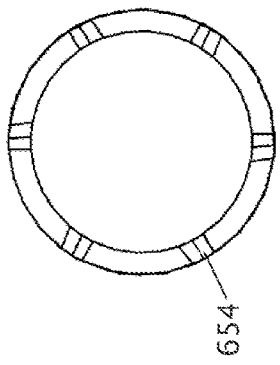
FIGS. 12A-12C depict various views of a first cutting tip configuration suitable for some embodiments of the present cannulas, such as those in the devices of FIGS. 8A-9B.
Figure 12B:
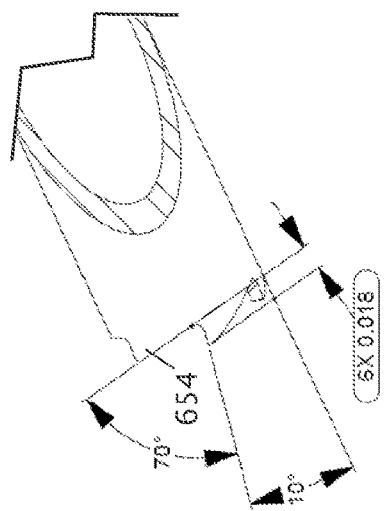
Figure 12A:
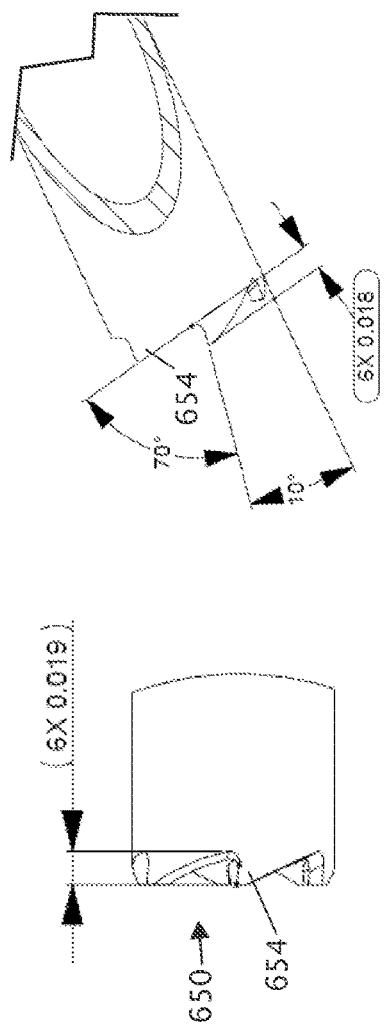

FIGS. 12A-12C depict various views of a first cutting tip configuration suitable for some embodiments of the present cannulas, such as those in the devices of FIGS. 8A-9B. For example, FIGS. 12A-12C depict the configuration of a cutting tip 650 used on end 111c of cannula 110c, and of end 111d of cannula 110d (with the only difference being the diameter of the respective cannula and corresponding cutting tip. Tip 650 comprises a sawtooth configuration with a plurality of (e.g., six, as in the depicted embodiment) cutting teeth 654. In this embodiment, tip 650 has a circular cross-sectional shape. Various dimensions are depicted in inches, which are accurate for at least some embodiments of an eleven (11) gauge cannula, and which may be proportionally scaled down for a thirteen (13) gauge needle. In some embodiments, cannula 110c includes an internal thread (e.g., as depicted in, and described in with reference to, FIGS. 4A-4E of WO 2008/033874) to facilitate capture and removal of a bone marrow sample.

Figure 13C:
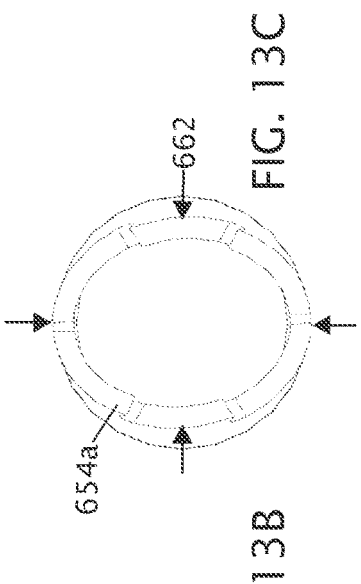
FIGS. 13A-13C depict various views of a second cutting tip configuration suitable for some embodiments of the present cannulas, such as those in the devices of FIGS. 8A-9B.
Figure 13B:
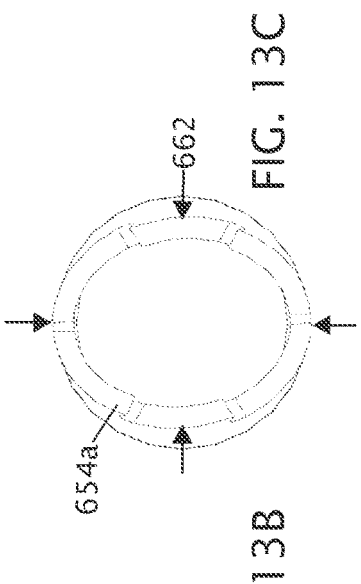
Figure 13A:

FIGS. 13A-13C depict various views of a first cutting tip configuration suitable for some embodiments of the present cannulas, such as the one in the device of FIG. 9A-9B. For example, FIGS. 13A-13C depict the configuration of a cutting tip 650a that may be used as an alternative to tip 650 on end 111d of cannula 110d. Tip 650a is similar to tip 650 in that tip 650a comprises a sawtooth configuration with a plurality of (e.g., six, as in the depicted embodiment) cutting teeth 654a. However, tip 650a differs from tip 650 in that tip 650a has a cross-sectional shape that is oval or that approximates an oval. More particularly; in the embodiment shown, tip 650 has a major transverse dimension 658 that is greater than and perpendicular to a minor transverse dimension 662, and both of major transverse dimension 658 and minor transverse dimension 662 are perpendicular to the central longitudinal axis of the cannula (e.g., 110d). Tip 650a is configured to be rotated in bone marrow to extract a sample of the bone marrow more effectively than at least some tips with circular cross-sectional shapes. In particular, as tip 654 rotates, minor transverse dimension 662 limits the diameter of the bone marrow sample at any given point. As tip 650a is inserted and rotated into the bone marrow, the bone marrow within cannula 110d may be compressed along a helical path traced by minor transverse dimension 662. However, once cannula 110d reaches its maximum depth into the bone marrow, minor transverse dimension 662 can be rotated in a single position to compress the innermost portion of the bone marrow sample, effectively narrowing and weakening the innermost portion of the sample to ease its removal. Additionally, the portions of the sample interior to cannula 110d have not been compressed to the same extent, and thereby resist removal from cannula 110d as cannula 110d is removed from the bone, increasing the likelihood that the sample will be completely withdrawn from the bone in a single piece. In some embodiments, tip 650a can be formed by compressing a tip 650 to decrease the diameter of a portion of tip 650 to minor transverse dimension 662 and correspondingly increasing the diameter of another portion of tip to major transverse dimension 658.

Figure 14:
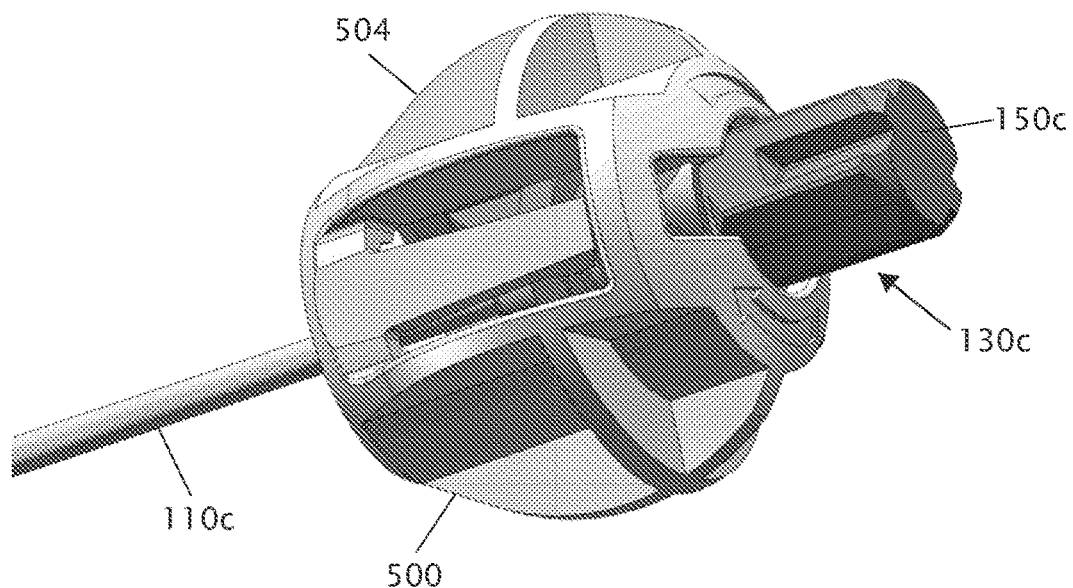
FIGS. 14-17 depict two perspective and two cross-sectional views of the handle of FIGS. 7A-7H coupled to various components of the IO devices of FIGS. 8A-9B.

FIGS. 14-17 depict two perspective and two cross-sectional views of the handle of FIGS. 7A-7H coupled to various components of the IO devices of FIGS. 8A-9B. In some embodiments of the present methods, needle set 100c (e.g., hub assembly 130c) FIGS. 8A-8B) can be coupled to a powered driver (e.g., driver 200 of FIG. 2) via a coupler (e.g., coupler 250a, as indicated in FIGS. 3, 5, and 6A). Needle set 100c can then be rotated by the powered driver and driven through the hard, outer cortical or compact layer of a bone (e.g., a pelvis, via the iliac crest) and/or into the cancellous or spongy portion of the bone. Once through the cortical layer, the coupler can be removed or de-coupled from hub assembly 130c of needle set 100c, and handle 500 can be coupled to the needle assembly by pressing body 504 of handle 500 over hub assembly 130c such that hub assembly 130c extends into passage 516 (passage 536) and projections 556 "snap" and extend into groove 608c of hub 140c to resist removal of hub assembly 130c from handle 500, as shown in FIG. 14. Needle assembly 100c can then be manipulated by a user via handle 500 to position end 101 of the needle set at a desired position within the bone. Once the needle set is positioned as desired, handle 500 can be removed from hub assembly 130c by pulling handle 500 away from needle set 100c until arms 560 flex to permit projections 556 to exit groove 608c. Hub 150c can then be rotated counter-clockwise relative to hub 140c to unscrew the threads of the respective Luer lock connectors and hub 150c and stylet 120 then removed.

Figure 15:
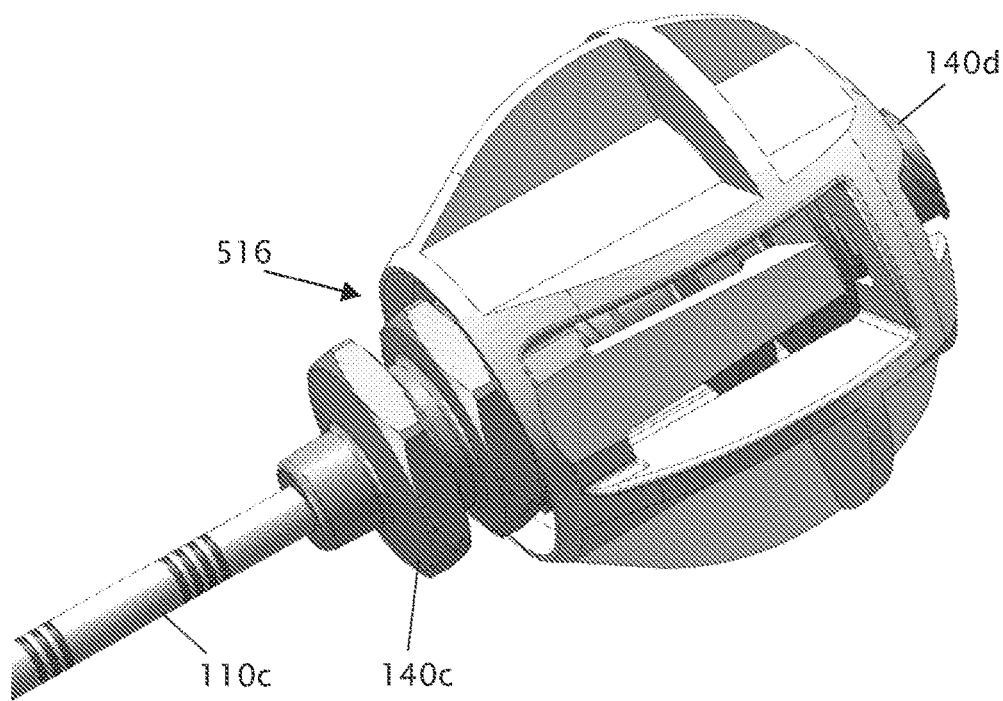
Figure 16:
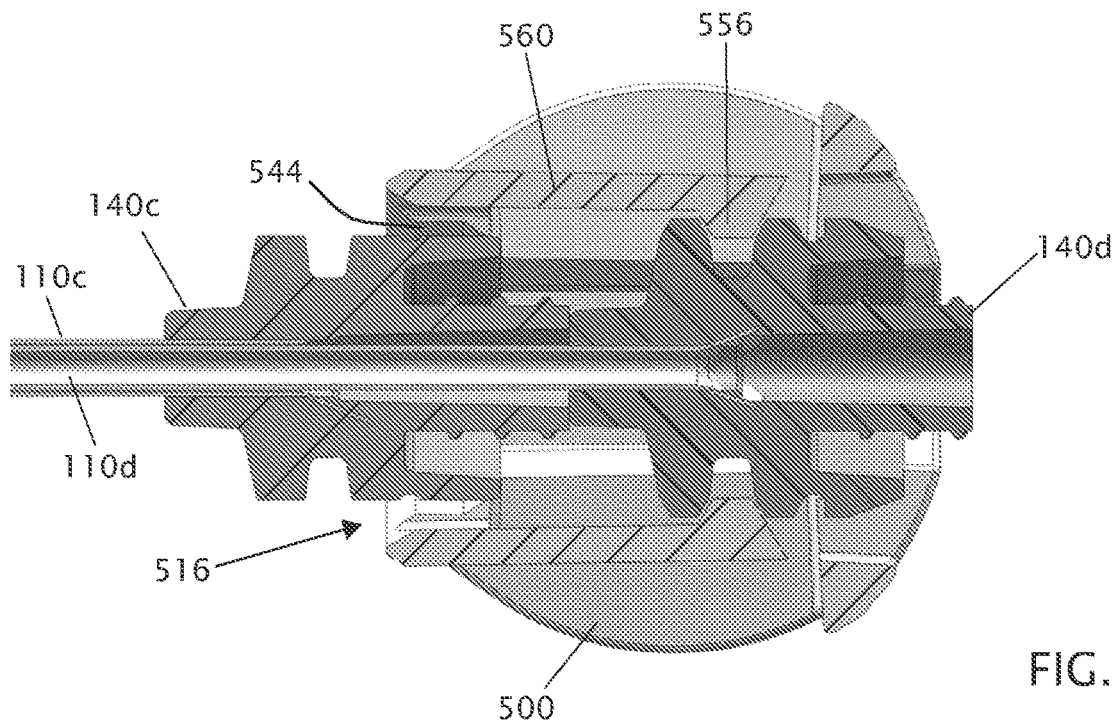

Before or after cannula 110d is inserted into cannula 110d, as shown in FIGS. 10-11 and 15-17, handle 500 can be coupled to cannula 110d by pressing body 504 of handle 500 over hub 140d such that hub 140d extends into passage 516 (passage 536) and projections 556 "snap" and extend into groove 608d of hub 140d to resist removal of hub 140d from handle 500, as shown in FIGS. 15 and 16. Cannula 110d can then be manipulated by a user via handle 500 to extend end 111d to a desired position (e.g., beyond end 111c of cannula 110c) to obtain a bone marrow sample (e.g., by rotating handle 500 and thereby rotating cannula 110d). Once a bone-marrow sample is obtained, cannula 110d can be removed from cannula 110c, handle 500 removed from cannula 110d by pulling handle away from hub 140d, and/or the bone marrow sample removed from cannula 110d (e.g., with an ejector and a funnel depicted in, and described in with reference to, FIGS. 9A-9B of WO 2008/033874). Handle 500 can then be re-coupled to hub 140c and cannula 110c repositioned (with or without trocar 120 disposed in cannula 110c) within the same hole in the cortical layer of bone, and the process repeated to obtain additional samples. Alternatively, cannula 110c can be removed from the bone altogether (with or without trocar 120 disposed in cannula 110c) using handle 500 and/or the powered driver (coupled to the hub or hub assembly by the coupler), at which point, the procedure may be terminated or needle set 100c can be re-inserted into the same or a different bone at a different position to obtain additional samples.

Figure 17:
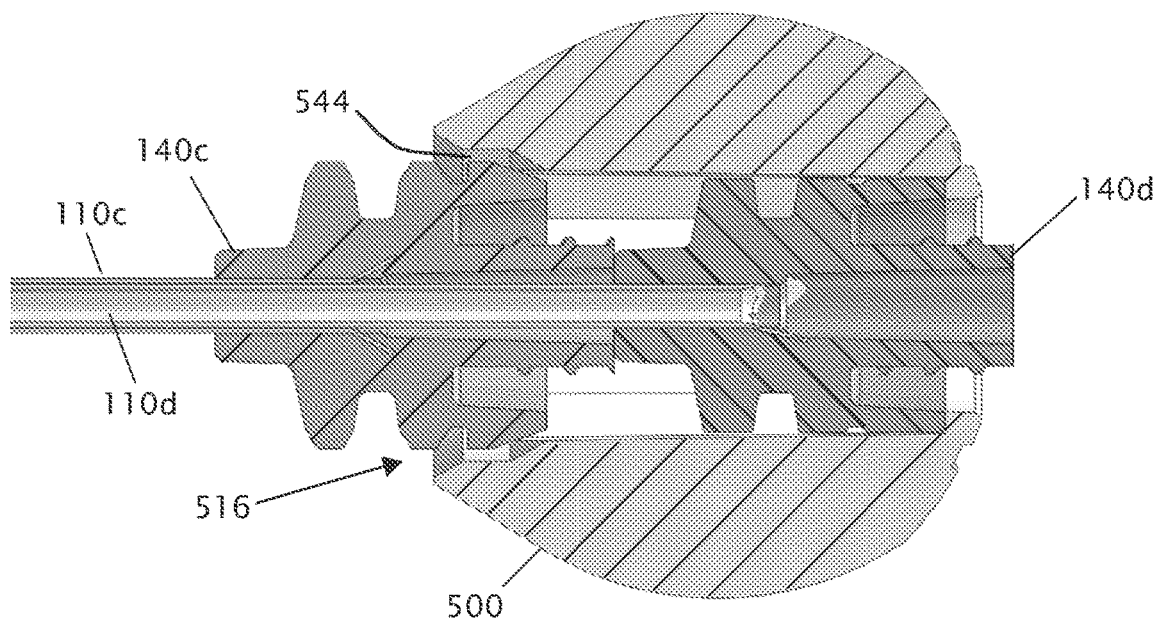

As depicted in FIGS. 16 and 17, in this embodiment, entry portion 544 of passage 516 in handle 500 is configured to permit handle 500 to rotate around hub 140c (diameter 548 of entry portion 544 is larger than the maximum transverse dimension of hub 140c) when handle 500 is coupled to hub 140d and cannula 110d is fully inserted into cannula 110c. This permits a user to rotate cannula 110d relative to 110c to obtain a bone marrow sample.

Figure 18:
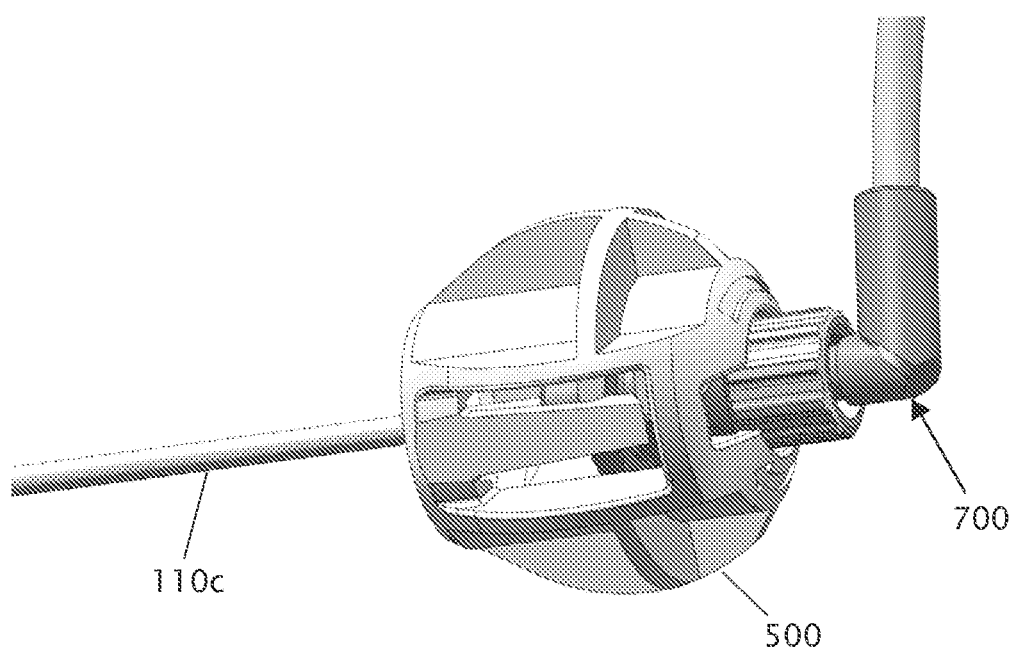
FIG. 18 depicts a perspective view of the handle of FIGS. 7A-7H coupled to the cannula of the IO device of FIGS. 8A and 8B, with the cannula coupled to a fluid source.

Additionally, and as depicted in FIG. 18, handle 500 (passage 516 at second end 512) can be configured to permit a fluid source or suction source to be coupled to the Luer lock of hub 140c or hub 140d even when the handle is coupled to the hub. This can be especially useful when it is desirable to obtain a fluid sample from the interior of a bone, and a connector (e.g., a right angle connector 700) can be coupled to the Luer lock of either of hub 140c or 140d at any of the points discussed above when the corresponding cannula is disposed in the bone, and trocar 120 is not disposed in cannula 110c. Right angle connector 700 can then be coupled to a syringe and liquid (e.g., blood) drawn through the respective cannula.

Figure 19:
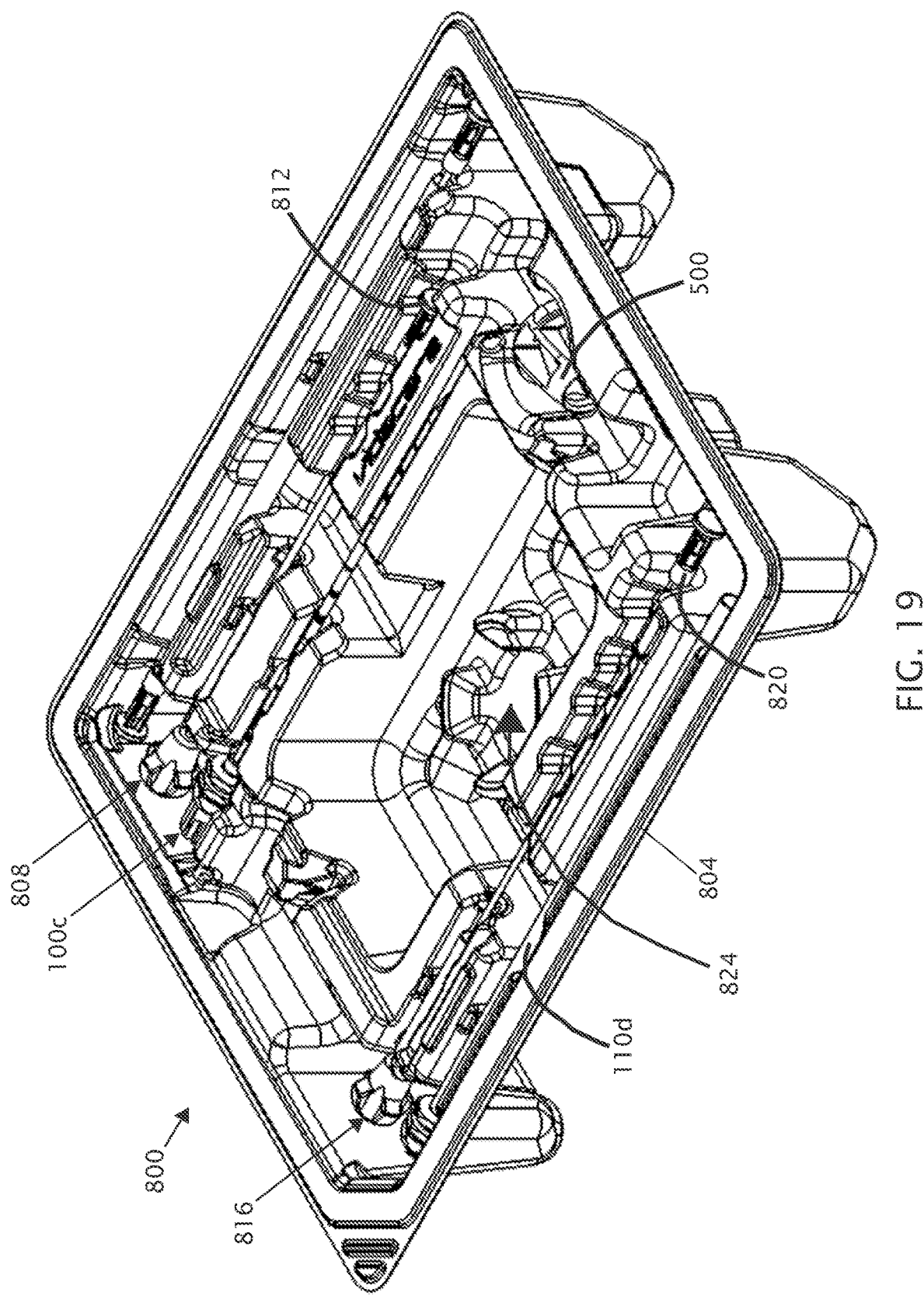
FIGS. 19 and 20 depict perspective and top views, respectively, of one embodiment of the present medical procedure trays comprising one of the present snap handles, one of the IO devices of FIGS. 8A-8B, and one of the IO devices of FIGS. 9A-9B.
Figure 20:
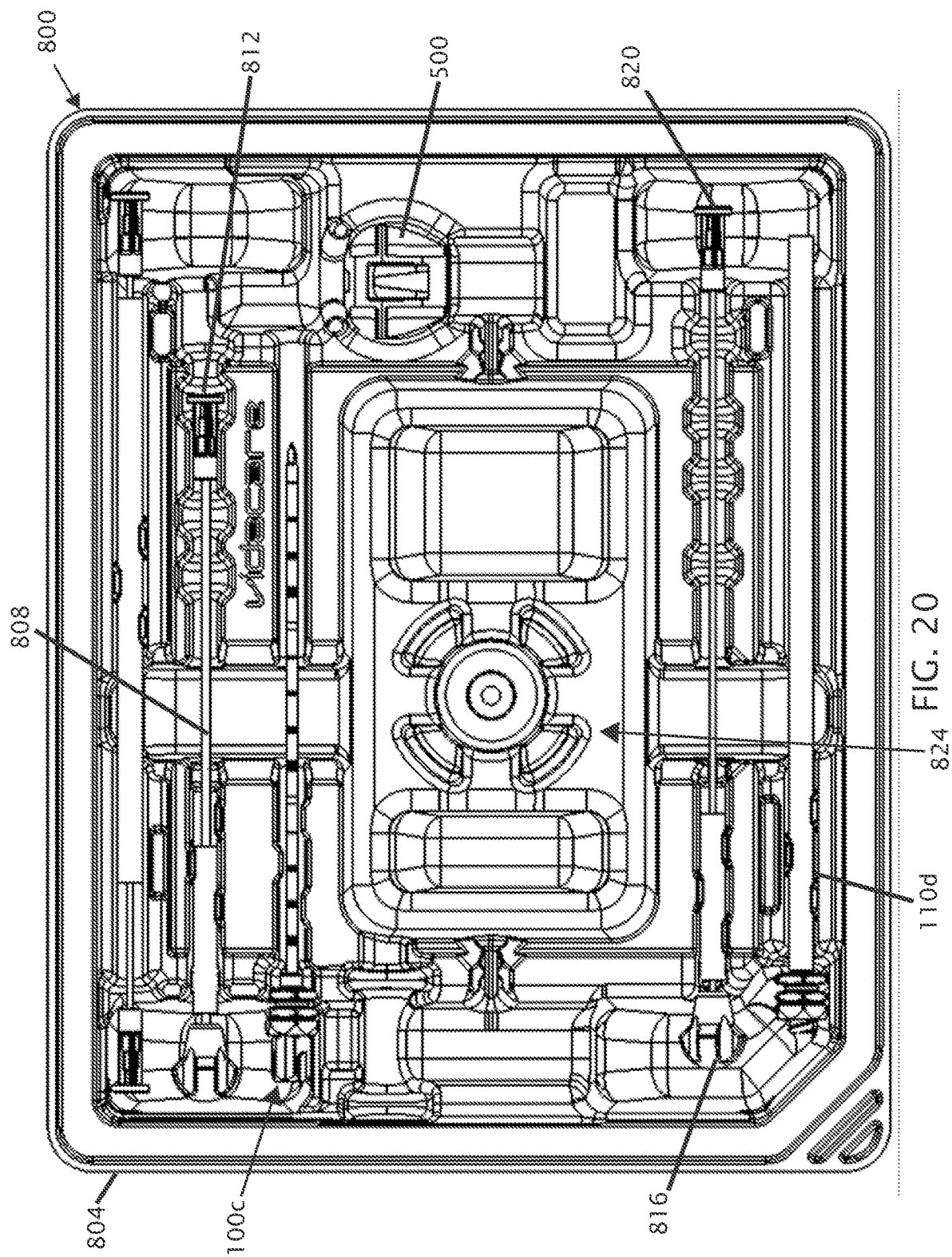

FIGS. 19 and 20 depict perspective and top views, respectively, of one embodiment of the present medical procedure trays or kits 800 comprising one of the present handles 500, one of the IO devices (needle set 100c) of FIGS. 8A-8B, and one of the IO devices (cannula 110d) of FIGS. 9A-9B. FIG. 21 depicts an exploded perspective view of tray 800. In the embodiment shown, tray or kit 800 comprises a polymer tray 800 having various recess sized to receive the components of the kit. In the embodiment shown, kit 800 further includes a first ejector 808 and funnel 812 (e.g., similar to the ejector and the funnel depicted in, and described in with reference to, FIGS. 9A-9B of WO 2008/033874) that are sized to function with cannula 110c, and a second ejector 816 and funnel 820 (e.g., similar to the ejector and the funnel depicted in, and described in with reference to, FIGS. 9A-9B of WO 2008/033874) that are sized to function with cannula 110d. In this embodiment, tray 804 also includes an indentation configured to receive a coupler (e.g., a coupler and sterile bag (e.g., as depicted in, and described in with reference to, FIGS. 1E-1J of WO 2008/033874). Tray 800 can also be sealed with one or more sterile sheets or drapes as described in WO 2008/033874.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices are not intended to be limited to the particular forms disclosed. Rather, they include all modifications and alternatives falling within the scope of the claims, and embodiments other than the one shown may include some or all of the features of the depicted embodiment. For example, components may be combined as a unitary structure, and/or connections may be substituted (e.g., threads may be substituted with press-fittings or welds). Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. An apparatus comprising:
a handle configured to be removably coupled to a hub of an intraosseous device, the handle including a body having a distal end, a proximal end, and a passage through the body extending from the distal end to the proximal end, at least a portion of the passage having a non-circular cross-sectional shape configured to receive the hub and prevent the hub from rotating relative to the handle, the distal end of the body configured to receive the hub of the intraosseous device, the body including one or more resilient arms each having a first end coupled to the body, a second end extending from the first end toward the proximal end of the body, and a projection extending inward toward a rotational axis of the handle to resist removal of the hub when the hub is disposed in the passage, each of the one or more resilient arms configured to be deflected away from the rotational axis of the handle to permit insertion and removal of the hub, and each projection configured to flex the corresponding resilient arm outward relative to the rotational axis of the handle to permit the hub to withdraw from the passage when a user pulls the intraosseous device away from the handle.

2. The apparatus of claim 1, where a cross-sectional perimeter of the handle has a first transverse dimension that is perpendicular to a longitudinal axis of the passage, and a second transverse dimension that is perpendicular to the first transverse dimension, and where the first transverse dimension does not vary from the second transverse dimension by more than ten percent of the first transverse dimension.

3. The apparatus of claim 2, where the handle has a cross-sectional perimeter that is substantially circular.

4. The apparatus of claim 1, where the one or more resilient arms include two resilient arms on opposite sides of the passage, each of the two resilient arms having a length extending parallel to the longitudinal axis of the passage.

5. The apparatus of claim 1, where the non-circular cross section is hexagonal.

6. An apparatus for accessing bone comprising:
a first hub configured to be removably coupled to a driveshaft of a powered driver;
a cannula having a first end configured to penetrate bone, a second end coupled in fixed relation to the hub, and a channel extending between the first end and the second end; and
a handle configured to be removably coupled to the hub such that a user can grasp the handle to manipulate the cannula by hand, the handle having a body having a distal end and a proximal end, the body defining a passage extending from the distal end to the proximal end, the distal end of the body configured to receive the hub, a portion of the passage configured to prevent the hub from rotating relative to the handle, the body including a resilient arm having a projection extending inward toward a rotational axis of the handle to resist removal of the hub when the hub is disposed in the passage, the projection being closer to the proximal end of the body than to the distal end of the body, the resilient arm configured to be deflected away from the rotational axis of the handle to permit insertion and removal of the hub, and the projection configured to permit a user to remove the hub from the passage without first deflecting the resilient arm outward relative to the rotational axis of the handle;
where the hub is not configured to be simultaneously coupled to a driveshaft and the handle.

7. The apparatus of claim 6, where the first end of the cannula has an oval cross-sectional shape.

8. The apparatus of claim 6, where the hub has a connector and is coupled to the second end of the cannula such that the connector is in fluid communication with the channel of the cannula.

9. An apparatus for accessing bone comprising:
a first hub configured to be removably coupled to a driveshaft of a powered driver;
a first cannula having a first end configured to penetrate bone, a second end coupled in fixed relation to the hub, and a channel extending between the first end and the second end, the channel having a first inner transverse dimension;
a second hub configured to be removably coupled to a driveshaft of a powered driver;
a second cannula having a first end configured to extract a bone marrow sample, a second end coupled in fixed relation to the second hub, and a channel extending between the first end and the second end, the second cannula having an outer transverse dimension that is smaller than the inner transverse dimension of the channel of the first cannula such that the second cannula can be inserted into the channel of the first cannula and rotated relative to the first cannula; and
a handle configured to be removably coupled to the second hub such that a user can grasp the handle to manipulate the second cannula by hand, the handle including a body having a distal end and a proximal end, the handle defining a passage having an entry portion at the distal end of the body configured to permit the handle to rotate around the first hub when the handle is coupled to the second hub, the handle including one or more projections configured resist removal of the second hub when the second hub is disposed in the passage, each projection being closer to the proximal end of the body than to the distal end of the body;
where the second hub is not configured to be simultaneously coupled to a driveshaft and the handle.

10. The apparatus of claim 9, where the first end of the second cannula has an oval cross-sectional shape.

11. The apparatus of claim 9, where the second cannula has a length that is greater than a length of the first cannula.

12. The apparatus of claim 9, where the first hub has a connector and is coupled to the second end of the first cannula such that the connector is in fluid communication with the channel of the first cannula.

13. The apparatus of claim 12, where the second hub has a connector and is coupled to the second end of the second cannula such that the connector is in fluid communication with the channel of the second cannula.

14. The apparatus of claim 9, where the first hub has a hexagonal cross-section.

15. The apparatus of claim 9, where the second hub has a hexagonal cross-section.

16. The apparatus of claim 9, where the first hub has an outer surface defining one or more detents.

17. The apparatus of claim 9, where the second hub has an outer surface defining one or more detents.

18. The apparatus of claim 9, where the passage has a length and a portion of the passage has a non-circular cross-sectional shape; and where the one or more projections extend toward the center of the passage.

19. The apparatus of claim 18, where the interior region has a hexagonal cross-section.

20. The apparatus of claim 18, where the handle comprises:
one or more resilient arms, each having a first end coupled in fixed relation to the body, and a second end extending from the first end such that the second end is movable toward a rotational axis of the handle;
where the one or more projections are each coupled to different one of the second ends of the of the one or more resilient arms; and
where each of the resilient arms is configured to be deflected away from the rotation axis of the handle to permit insertion and removal of the hub.

21. The apparatus of claim 18, where the body further comprises a plurality of ribs.

22. The apparatus of claim 21, where the ribs comprise a plurality of longitudinal ribs extending parallel to the rotational axis of the handle, and at least one circumferential rib extending between longitudinal ribs.

23. The apparatus of claim 21, where each rib has a distal edge, and the ribs are configured such that a circle disposed in a plane that is perpendicular to the rotational axis contacts the distal edges of at least three ribs.

24. The apparatus of claim 18, where the handle has a first end and a second end, and the body defines an opening in the second end that has at least one transverse dimension that is smaller than a corresponding transverse dimension of the passage.

25. The apparatus of claim 24, where the entry portion is hollow and at the first end of the handle, the entry portion having a cross-sectional area that is larger than the cross-sectional area of the interior region.

26. The apparatus of claim 25, where the entry portion has a circular cross-section.

* * * * *